(12) United States Patent
Rigas

(10) Patent No.: US 12,295,964 B2
(45) Date of Patent: *May 13, 2025

(54) TREATING PAIN ASSOCIATED WITH CHEMOTHERAPY-INDUCED PERIPHERAL NEUROPATHY

(71) Applicant: MEDICON PHARMACEUTICALS, INC., Setauket, NY (US)

(72) Inventor: Basil Rigas, Setauket, NY (US)

(73) Assignee: MEDICON PHARMACEUTICALS, INC., Setauket, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/515,734

(22) Filed: Nov. 21, 2023

(65) Prior Publication Data

US 2024/0180936 A1 Jun. 6, 2024

Related U.S. Application Data

(63) Continuation of application No. PCT/US2022/072496, filed on May 23, 2022.

(60) Provisional application No. 63/192,246, filed on May 24, 2021.

(51) Int. Cl.
*A61K 31/683* (2006.01)
*A61P 25/02* (2006.01)

(52) U.S. Cl.
CPC ............ *A61K 31/683* (2013.01); *A61P 25/02* (2018.01)

(58) Field of Classification Search
CPC ...... A61K 31/661; A61K 31/683; A61P 25/02
See application file for complete search history.

(56) References Cited

U.S. PATENT DOCUMENTS

| | | |
|---|---|---|
| 8,236,820 B2 | 8/2012 | Rigas |
| 2006/0241074 A1 | 10/2006 | Woolf |
| 2013/0225529 A1 | 8/2013 | Rigas |
| 2024/0100073 A1 | 3/2024 | Rigas |

FOREIGN PATENT DOCUMENTS

| | | | |
|---|---|---|---|
| CN | 101820755 | 9/2010 | |
| CN | 105658651 | 6/2016 | |
| WO | 2013067591 | 5/2013 | |
| WO | WO-2017106714 A1 * | 6/2017 | ........... A61K 31/192 |
| WO | 2018064354 | 4/2018 | |
| WO | 2019067919 | 4/2019 | |
| WO | 2020101790 | 5/2020 | |
| WO | 2022251805 | 12/2022 | |
| WO | 2022251806 | 12/2022 | |

OTHER PUBLICATIONS

Argyriou, A. etal., "Bortezomib-induced peripheral neuropathy in multiple myeloma: a comprehensive review of the literature", Blood, Am Soc Hematol., 112(5):1593-9, (2008).

Bagdas, D. et al., "The role of alpha5 nicotinic acetylcholine receptors in mouse models of chronic inflammatory and neuropathic pain", Biochem Pharmacol., 97(4):590-600, (2015).

Bonin, R. et al., "A simplified up-down method (SUDO) for measuring mechanical nociception in rodents using von Frey filaments", Mol Pain, 10:26, (2014).

Carozzi, V. et al., "Neurophysiological and neuropathological characterization of new murine models of chemotherapy-induced chronic peripheral neuropathies", Exp Neurol., 226(2):301-9, (2010).

Chaplan, S. et al., "Quantitative assessment of tactile allodynia in the rat paw", J Neurosci Methods, 53(1):55-63, (1994).

Colvin, L., "Chemotherapy-induced peripheral neuropathy: where are we now?", Pain, 160 Suppl 1(Suppl 1):S1-S10, (2019).

Currie, G. et al., "Animal models of chemotherapy-induced peripheral neuropathy: A machine-assisted systematic review and meta-analysis", PLOS Biol., 17(5):e3000243, (2019).

Eldridge, S. et al., "A Comparative Review of Chemotherapy-Induced Peripheral Neuropathy in In Vivo and In Vitro Models", Toxicol Pathol., 48(1):190-201, (2020).

Hidaka, T. et al., "Herbal medicine Shakuyaku-kanzo-to reduces paclitaxel-induced painful peripheral neuropathy in mice", Eur J Pain, 13(1):22-7, (2009).

International Application No. PCT/US2022/072496; International Search Report and Written Opinion of the International Searching Authority, date of mailing Sep. 2, 2022; 10 pages.

Kaley, T. et al., "Therapy of chemotherapy-induced peripheral neuropathy", Br J Haematol., 145(1):3-14, (2009).

MacKenzie, G. et al., "Phospho-sulindac (OXT-328), a novel sulindac derivative, is safe and effective in colon cancer prevention in mice", 139(4):1320-32, (2010).

Matteolabakis, G. et al., "Topically applied phospho-sulindac hydrogel is efficacious and safe in the treatment of experimental arthritis in rats", Pharm Res., 30(6):1471-82, (2013).

Moore, R. et al., "Single dose oral analgesics for acute postoperative pain in adults—an overview of Cochrane reviews (Review)", Cochrane Database Syst Rev., 2015(9):CD008659, pp. 1-36, (2015).

Toma, W. et al., "Effects of paclitaxel on the development of neuropathy and affective behaviors in the mouse", Neuropharmacology, 117:305-15, (2017).

Wen, Z. et al., "The ocular pharmacokinetics and biodistribution of phospho-sulindac (OXT-328) formulated in nanoparticles: Enhanced and targeted tissue drug delivery", Int J Pharm., 557:273-9, (2019).

Xie, G. et al., "The metabolism and pharmacokinetics of phospho-sulindac (OXT-328) and the effect of difluoromethylornithine", Br J Pharmacol., 165(7):2152-66, (2012).

Dobretsov, M. et al., "Animal Models of Diabetic Neuropathic Pain", Curr Protoc Neurosci., 29(1):147-69, (2011).

International Application No. PCT/US2022/072497; International Preliminary Report on Patentability, date of issuance Dec. 7, 2023, 7 pages.

International Application No. PCT/US2022/072497; International Search Report and Written Opinion of the International Searching Authority, date of mailing Sep. 2, 2022; 10 pages.

Morrow, T et al., "Animal Models of Painful Diabetic Neuropathy: The STZ Rat Model", Curr Prot Neurosci., 9(18):1-11, (2004).

U.S. Appl. No. 18/515,743; Final Office Action, dated Sep. 16, 2024; 9 pages.

(Continued)

*Primary Examiner* — Kara R McMillian

(74) *Attorney, Agent, or Firm* — Weaver Austin Villeneuve & Sampson LLP

(57) ABSTRACT

The invention features methods of preventing and/or treating neuropathic pain associated with chemotherapy-induced peripheral neuropathy (CIPN).

37 Claims, 9 Drawing Sheets

(56) References Cited

OTHER PUBLICATIONS

U.S. Appl. No. 18/515,743; Non-Final Office Action, dated Jun. 24, 2024; 9 pages.
Zochodne, D et al., "The Influence of Sulindac on Experimental Streptozotocin-Induced Diabetic Neuropathy", Can J Neur Sci., 21(3):194-202, (1994).

* cited by examiner

CIPN Treatment

FIG. 11(contd)
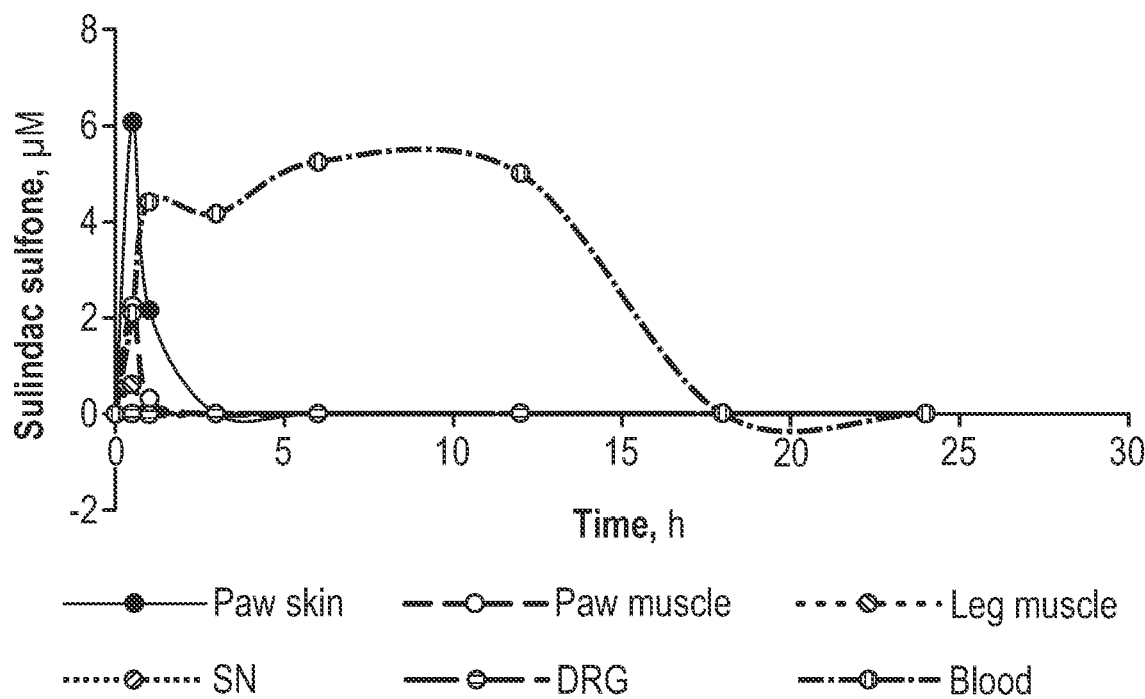
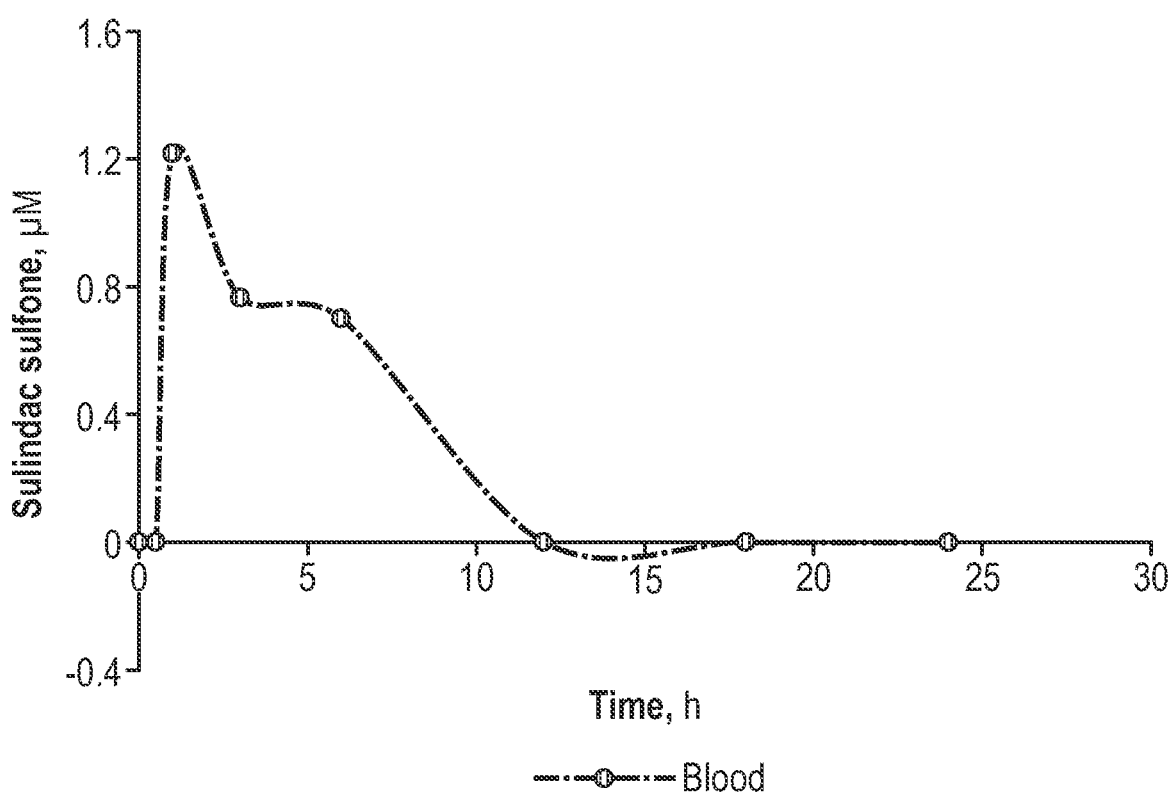

TREATING PAIN ASSOCIATED WITH CHEMOTHERAPY-INDUCED PERIPHERAL NEUROPATHY

This application is a bypass continuation of International Application No. PCT/US2022/072496, filed May 23, 2022, which claims the benefit of U.S. provisional application 63/192,246, filed May 24, 2021, the complete contents of which are incorporated herein by reference for all purposes.

FIELD OF THE INVENTION

The invention relates to compounds and their use in the treatment of neuropathic pain associated with chemotherapy-induced peripheral neuropathy (CIPN).

BACKGROUND OF THE INVENTION

Neuropathies are diseases or abnormalities of the nervous system, which afflict more than 20 million Americans. Indeed, according to recent studies, it is observed that neuropathic pain affects about 1 in every 10 adults and the economic burden for treating this pain is increasing.

Neuropathies are associated with the development of neuropathic pain. Neuropathic pain can occur as a result of damage to the peripheral or central nervous system. Peripheral neuropathic pain is caused by damage to nerve structures such as peripheral nerve endings or nociceptors which become extremely sensitive to stimulation and which can generate pulses in the absence of stimulation. The damage can occur for many reasons, such as chemotherapy treatments (i.e., CIPN), diseases such as diabetes, as well as advanced-stage cancers, viruses (e.g., herpes zoster or HIV), and physical injury (e.g., an accident or surgery).

The lesion of the peripheral nerve can result in pathological states characterized by the presence of continuous spontaneous pain often associated with hyperalgesia (increased response to harmful stimuli) and allodynia (pain induced by a non-painful stimulus). Hyperalgesia and allodynia have been linked to central sensitisation, in which CNS nociceptive neurons display increased excitability due to a reduced stimulation threshold, triggered by persistent input or peripheral injury. Central sensitisation is implicated in the generation and maintenance of neuropathic pain associated with peripheral neuropathies.

From a symptomatic perspective, peripheral neuropathies may cause sharp pains, dull aches, a sensation of painful burning or cold, paraesthesia, a loss of proprioception, numbness, or even a loss of the sensation of pain.

There is currently a worldwide need for additional pain therapy, and neuropathic pain has developed into a major health problem in broad areas of the population.

Treatment of neuropathic pain is often attempted using so-called unconventional analgesics such as antidepressants like duloxetine and amitriptyline, or anti-epileptics like gabapentin or pregabalin. Additionally, topical anaesthetics, including lidocaine, have been used for the treatment and management of neuropathic pain. Despite evidence to the contrary, nonsteroidal anti-inflammatory drugs (NSAIDs) are widely used in the management of neuropathic pain. Upon a review of recent clinical trials, however, there was no indication of any significant pain reduction with NSAIDs in neuropathic pain patients (Moore et al. Cochrane Database of Systematic Reviews (2015); 10: 1-25), with no clinical outcome showing a statistically significant difference between NSAIDs and placebo. The Cochrane Library concluded that NSAIDs should not be recommended for the treatment of neuropathic pain.

CIPN, and the associated neuropathic pain, is a frequent, dose-dependent side effect of commonly used chemotherapies. Peripheral nerve damage represents the majority of neurological damage associated with chemotherapy toxicity and represents the most frequent limiting factor for chemotherapy after hematological toxicity. The pain has been thought to be due to a direct toxic effect on the sensory axon, demyelination, or an impairment of calcium metabolism. The neuropathic pain associated with CIPN is particularly difficult to treat. It is currently managed with antidepressants (e.g., duloxetine) and/or antiepileptics (e.g., gabapentin and pregabalin). Unfortunately, pain control is not very satisfactory and these systemic treatments induce major side effects leading to poor treatment adherence. Indeed, to date, there are no satisfactory means of preventing or even treating the pain associated with CIPN: the only approved drug (duloxetine) is generally considered ineffective.

Therefore, there is a strong need for compounds that treat and/or prevent pain associated with peripheral neuropathies, in particular CIPN.

SUMMARY OF THE INVENTION

The inventor has surprisingly found that phosphosulindac (PS) is effective in the treatment and prevention of pain associated with CIPN.

PS is a non-steroidal compound with anti-inflammatory activity. However, unlike its parent compound, the NSAID sulindac, PS does not inhibit COX-1 and COX-2 expression and so is not a typical NSAID. PS has previously been shown to have anti-cancer and anti-inflammatory properties via its inhibition of activation of NF-κB and changes in MAPK signalling branches, as well as an activity in treating rheumatoid arthritis in inflammatory mouse models via suppression of key pro-inflammatory signalling pathways (Mackenzie et al. (2010) *Gastroenterology* 139(4): 1320-32 and Mattheolabakis et al. (2013) *Pharm Res* 30(6): 1471-82). WO 2019/067919 suggests an anti-inflammatory activity of PS in an acute model of dry eye disease (DED). Furthermore, in this model, PS is seen to restore suppressed ocular sensitivity in DED, suggesting a role of PS in increasing rather than reducing nociception. Although PS is not a typical NSAID as noted above, it demonstrated similar activity to NSAIDs when administered to normal eyes in the DED model. However, these observations fail to suggest a role for PS in the treatment of neuropathic pain associated with CIPN. Furthermore, clinical guidance in the field recommends avoiding the use of NSAIDs for the treatment of all types of neuropathic pain, and so anti-inflammatory activity alone is considered not sufficient therapeutically.

Nevertheless, the present inventor considered the activity of PS in a specific animal model of neuropathic pain and demonstrated a surprising therapeutic efficacy, equivalent to direct acting nerve blocking anaesthetics, e.g., lidocaine and pregabalin. Specific animal models are important during the development of therapies for treating neuropathic pain. Indeed, given the pathogenesis of pain associated with peripheral neuropathy, observations of efficacy of a particular compound in an alternative pain model cannot indicate the utility of that compound in treating neuropathic pain. In line with this, it is not possible to extrapolate the use of effective drugs from other forms of neuropathic pain to the neuropathic pain of particular interest, even if the clinical syndrome is similar. For example, gabapentin shows different efficacy in the treatment of different forms of neuropathic pain. Accordingly, the animal model used in early testing before further clinical development is crucial. Based on the specific animal model of CIPN neuropathic pain, the observations herein demonstrate an unprecedented efficacy of PS in the treatment and/or prevention of neuropathic pain associated with CIPN.

Therefore, in a first aspect, the invention provides a method of treating and/or preventing neuropathic pain associated with CIPN comprising administering a therapeutically effective amount of PS to a subject in need thereof such that neuropathic pain associated with CIPN is treated and/or prevented.

In some embodiments, the PS is the sulfoxide form of PS. Therefore, the PS may have the formula I (PS-I):

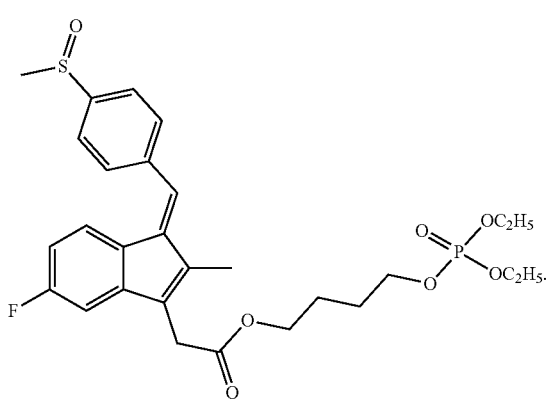

(I)

In other embodiments, the PS is the sulfide form of PS. Therefore, the PS may have the formula II (PS-II):

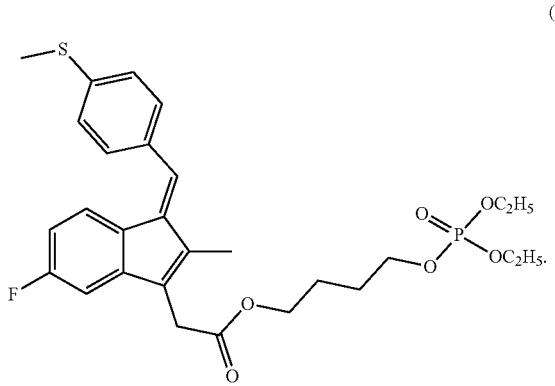

(I)

Herein, references to 'phosphosulindac' or to 'PS' encompass both PS-I and PS-II. The sulfide form of the compound is preferred. The compounds of formulae I and II are described in U.S. Pat. No. 8,236,820, which is hereby incorporated by reference in its entirety.

As noted above, nerve damage associated with CIPN may result in over-activation of pain signalling pathways resulting in sensitisation of peripheral and/or central neurons, which display reduced stimulation thresholds. Accordingly, subjects having CIPN may experience pain as a consequence of this sensitisation, for example, experiencing pain induced by a non-painful stimulus (allodynia) or experiencing heightened pain in response to a harmful stimulus (hyperalgesia). On the basis of the observations herein, PS may have a direct analgesic effect, for example by reducing the neuronal signalling involved in the sensation of pain. Furthermore, PS may reduce pain generated via peripheral sensitisation or via central sensitisation. Accordingly, PS may reduce or prevent pain signalling occurring centrally. The PS may reduce or prevent pain signalling occurring in the sciatic nerve. The PS may reduce or prevent pain signalling occurring in the dorsal root ganglion. Given that PS is shown to ascend peripheral neurons towards the spinal cord, PS may reduce or prevent pain signalling occurring in the spinal cord. In some embodiments, the neuropathic pain is allodynia. The allodynia may be in response to mechanical and/or thermal stimuli. In addition, in some embodiments, the neuropathic pain is hyperalgesia.

PS may be formulated into a pharmaceutical composition for use in the invention. In some embodiments, the pharmaceutical composition comprises PS and one or more pharmaceutically acceptable excipients. PS may be formulated for topical administration, in particular for topical administration to a subject's upper and lower limbs (i.e., to cover the stocking and glove distribution).

BRIEF DESCRIPTION OF THE FIGURES

FIG. 12A concerns mechanical allodynia (*, statistically significant differences; NS, not statistically significant). FIG. 12B concerns cold allodynia (values: Mean±SEM; *, $p<0.0001$).

DETAILED DESCRIPTION OF THE INVENTION

Definitions

Figure 1:
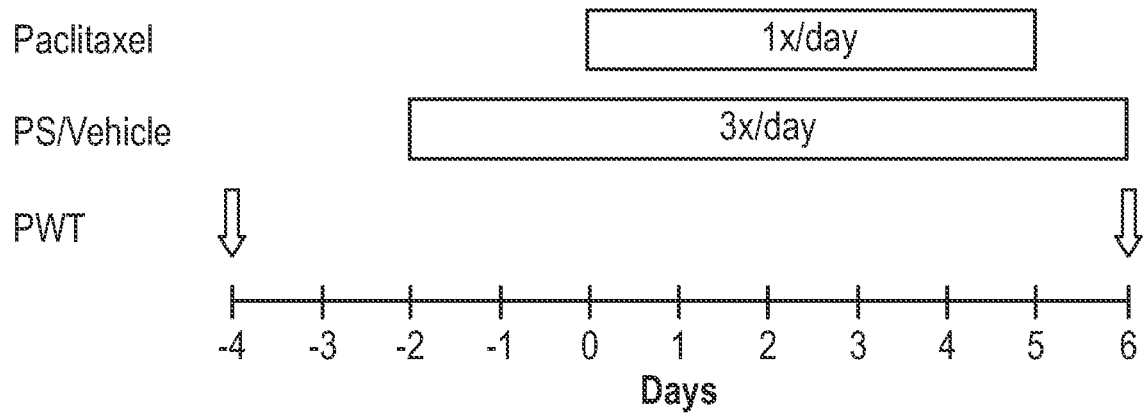
FIG. 1—schematic outline of the neuropathic pain associated with CIPN prevention study. PWT is paw withdrawal threshold test.

The following definitions of types of pain are according to the International Association for the Study of Pain (IASP). "Pain" is an unpleasant sensory and emotional experience associated with, or resembling that associated with, actual or potential tissue damage. "Neuropathic pain" is caused by a lesion or disease of the somatosensory nervous system. Neuropathic pain is a clinical description (and not a diagnosis) which requires a demonstrable lesion or a disease that satisfies established neurological diagnostic criteria. Patients with neuropathic pain may experience one or more sensations described as heat, burning, throbbing, shooting, stabbing, sharpness, cramping, aching, tingling, numbness, or pins and needles. The term "lesion of the somatosensory nervous system" is commonly used when diagnostic investigations (e.g., imaging, neurophysiology, biopsies, lab tests) reveal an abnormality or when there was obvious trauma. The term "disease of the somatosensory nervous system" is commonly used when the underlying cause of the lesion is known (e.g., stroke, vasculitis, diabetes mellitus, genetic abnormality). "Peripheral neuropathic pain" is pain caused by a lesion or disease of the peripheral somatosensory nervous system. "Central neuropathic pain" is pain caused by a lesion or disease of the central somatosensory nervous system. "Central sensitisation" refers to increased responsiveness of nociceptive neurons in the central nervous system to their normal or subthreshold afferent input. "Peripheral sensitisation" refers to increased responsiveness and reduced threshold of nociceptive neurons in the periphery to the stimulation of their receptive fields. "Allodynia" is pain due to a stimulus that does not normally provoke pain. "Hyperalgesia" is increased pain from a stimulus that normally provokes pain.

In general, the term "disease" refers to a state of being or health status of a patient or subject capable of being treated using the methods provided herein.

The term "therapeutically effective amount" refers to that amount of a compound or combination of compounds as described herein that is sufficient to effect the intended application including, but not limited to, treating and/or preventing the disease.

"Pharmaceutically acceptable excipient" is intended to include any and all solvents, dispersion media, coatings, antibacterial and antifungal agents, isotonic and absorption delaying agents, and inert ingredients included in pharmaceutical compositions. The use of such pharmaceutically acceptable excipients for formulating active pharmaceutical ingredients is well known in the art. Except insofar as any conventional pharmaceutically acceptable excipient is incompatible with PS, its use in the therapeutic compositions of the invention is contemplated.

Use of the term "about" when referring to a number is optional, and means that the number referred to is an approximation within typical experimental variability (or within statistical experimental error), and thus the number may vary accordingly.

The term "comprising" encompasses "including" as well as "consisting", e.g., a composition "comprising" X may consist exclusively of X or may include something additional (e.g., X+Y).

Pain Associated with Chemotherapy-Induced Peripheral Neuropathy

As outlined above, chemotherapy can cause damage to neurons resulting in peripheral neuropathy and associated neuropathic pain. The pain can arise during or after a patient has undergone chemotherapy and can manifest for example as shooting, burning, or stabbing pain associated with other sensory symptoms. Accordingly, in some embodiments, the invention provides a method of preventing neuropathic pain associated with CIPN comprising administering a therapeutically effective amount of PS to a subject in need thereof such that neuropathic pain associated with CIPN is prevented. In other embodiments, the invention provides a method of treating neuropathic pain associated with CIPN, comprising administering a therapeutically effective amount of PS to a subject in need thereof such that neuropathic pain associated with CIPN is treated. A subject may experience neuropathic pain caused by one or more previous doses of chemotherapy in advance of one or more subsequent doses and so the subject would benefit from an analgesic which can both treat existing neuropathic pain and prevent generation of further neuropathic pain. Therefore, in some embodiments, PS can be used in the treatment and prevention of neuropathic pain associated with CIPN. In line with the above, the invention provides PS for use in the treatment and/or prevention of neuropathic pain associated with CIPN. Furthermore, the invention provides the use of PS for the manufacture of a medicament for the treatment and/or prevention of neuropathic pain associated with CIPN.

As CIPN develops in light of chemotherapy, the subject may be a human patient with cancer, who is about to receive treatment, is receiving treatment, has previously received treatment with one or more chemotherapeutic compounds. In general, a chemotherapeutic compound refers to an agent having antineoplastic properties or the ability to inhibit the growth or proliferation of cells. The prevalence of CIPN is agent-dependent, with reported rates varying from 19% to more than 85% in patients on different medications, and is the highest in the case of platinum-based drugs, taxanes, immunomodulatory drugs, and epothilones, although it is also observed in patients on other common cancer chemotherapies, including vinca alkaloids and proteasome inhibitors. Therefore, the one or more chemotherapeutic compounds may be a platinum-based antineoplastic (for example oxaliplatin, cisplatin, or carboplatin), a taxane (for example paclitaxel, docetaxel, or cabazitaxel), a vinca alkaloid (for example vincristine, vinblastine, vinorelbine, or vindesine), or a proteasome inhibitor (for example, bortezomib). The one or more chemotherapeutic compounds may be one or more immunomodulatory drugs, including thalidomide and/or its analogues. The one or more chemotherapeutic compounds may be a platinum-based antineoplastic, for example oxaliplatin, a taxane, for example paclitaxel, and a vinca alkaloid, for example vincristine. The subject may have any cancer which is treated with a chemotherapeutic compound associated with the occurrence of CIPN and the associated neuropathic pain. In some embodiments, the subject with CIPN has a solid tumor cancer. The subject may have ovarian cancer, breast cancer, lung cancer (for example non-small cell lung cancer), Kaposi sarcoma, and/or pancreatic cancer. Alternatively, the subject may have melanoma, esophageal cancer, prostate cancer (for example hormone-refractory prostate cancer), head and neck cancer, stomach cancer, and/or cervical cancer.

On the basis of the observations herein, PS has a direct analgesic effect on neuropathic pain associated with CIPN. The neuropathic pain associated with CIPN may be a burning pain. A subject undergoing or following chemotherapy may experience neuropathic pain constantly present and symmetric in the lower and upper limbs. In treating neuropathic pain associated with CIPN, PS may reduce or eliminate the neuropathic pain. In treating the neuropathic pain associated with CIPN, the PS may also reduce or eliminate one or more of the sensory symptoms associated with CIPN. In preventing neuropathic pain associated with CIPN, PS may decrease the incidence of the neuropathic pain. In preventing neuropathic pain associated with CIPN, the PS may also decrease the incidence of one or more of the sensory symptoms associated with CIPN.

Patients suffering from CIPN describe a range of sensory, bilateral symptoms, for example in hands and feet (also described as the 'stocking and glove' distribution). The sensory symptoms include paresthesia (e.g., numbness, tingling, pricking, and/or formication), burning sensations, or shooting (i.e., electric shock-like) sensations. Even if the sensory symptoms experienced by a subject undergoing or following chemotherapy are not considered painful (or do not reach a threshold necessary to be considered pain per se), PS may reduce, eliminate, or decrease the incidence of, any one or more of the sensory symptoms experienced by a subject undergoing or following chemotherapy, including those listed above. PS can be used to reduce, eliminate, or decrease the incidence of, the stocking and glove distribution in a subject undergoing or following chemotherapy.

As noted above, the neuropathic pain associated with CIPN may be a consequence of central sensitisation resulting in allodynia and/or hyperalgesia. PS may reduce, eliminate, or decrease the incidence of the neuronal signalling involved in the sensation of pain in a subject undergoing or following chemotherapy. The PS may reduce, eliminate, or decrease the incidence of pain generated via peripheral sensitisation or via central sensitisation. Thus, the PS may reduce, eliminate, or decrease the incidence of pain signalling occurring centrally. The PS may reduce, eliminate, or decrease the incidence of pain signalling occurring in the sciatic nerve. The PS may reduce, eliminate, or decrease the incidence of pain signalling occurring in the dorsal root ganglion. Given that PS is shown to ascend peripheral neurons towards the spinal cord, PS may reduce, eliminate, or decrease the incidence of pain signalling occurring in the spinal cord. The neuropathic pain in a subject undergoing or following chemotherapy CIPN may be allodynia (e.g., mechanical or thermal allodynia). Additionally or alternatively, the neuropathic pain in a subject undergoing or following chemotherapy CIPN may be hyperalgesia.

Neuropathic pain in a patient undergoing or following chemotherapy can be measured on a visual analogue pain scale or using any other appropriate method in the art.

Pharmaceutical Compositions

The PS for use in the methods of the invention can be formulated into an appropriate pharmaceutical composition for administering to subjects with CIPN. Pharmaceutical compositions are typically formulated to provide a therapeutically effective amount of PS and may further comprise a pharmaceutically acceptable excipient.

Neuropathic pain associated with CIPN can occur at various sites on the body. However, as outlined above, CIPN tends to affect peripheral nerves in the upper and lower limbs, and thus the extremities, explaining the 'stocking and glove' distribution experienced by these patients. Therefore, a particularly useful pharmaceutical composition comprising PS is one which can be applied directly to peripheral locations experiencing neuropathic pain, for example the upper and lower limbs of the subject. In addition, the pharmaceutical composition comprising PS may be applied to those locations experiencing one or more sensory symptoms of CIPN. Accordingly, the pharmaceutical composition comprising PS may be formulated for topical administration. In particular, the pharmaceutical composition comprising PS may be formulated for dermal administration, in particular to the skin of the upper and/or lower limbs of the subject.

In some embodiments, the pharmaceutical composition comprising PS may be formulated as a semi-solid or liquid. Therefore, the pharmaceutical composition comprising PS may be formulated as a cream, gel (e.g., a hydrogel), lotion, ointment, foam, and/or spray. These compositions differ in their relative concentrations of oils and water, which causes the compositions to have different densities. Altering the density of the formulation is a way in which exposure of the affected area to the pharmaceutical composition can be controlled. For example, a less dense formulation, which requires rubbing in until it has been absorbed, may result in a shorter exposure time. Alternatively, a more dense formulation, which is not readily absorbed, may allow prolonged exposure of the area to the pharmaceutical composition. The skilled person is aware of formulating topical pharmaceutical compositions so as to modify the relative exposure of the area to the active pharmaceutical ingredient.

In other embodiments, the pharmaceutical composition comprising PS may be formulated as a patch which can be applied to the skin. The patch may be manufactured in such a way as to ensure controlled release of PS to the affected area.

Formulations suitable for topical administration and appropriate pharmaceutically acceptable excipients are well-known in the art. Exemplary formulations for topical administration are provided in WO 2019/067919, which is hereby incorporated by reference in its entirety.

In some embodiments, the formulation of PS suitable for topical administration may comprise PS at a concentration of about 0.5% w/w to about 15% w/w of the pharmaceutical composition. Accordingly, the PS may be at a concentration of 15%, 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, 1%, or 0.5% w/w of the pharmaceutical composition. As an illustrative example, when formulated as a topical cream, the PS may be at a concentration of less than or equal to 8% w/w of the pharmaceutical composition, for example about 5% w/w of the pharmaceutical composition, in particular about 3% w/w of the pharmaceutical composition. As a further illustrative example, when formulated as a gel, the PS may be at a concentration of less than or equal to 8% w/w of the pharmaceutical composition, for example less than or equal to 5% w/w of the pharmaceutical composition, in particular less than or equal to 3% w/w of the pharmaceutical composition, for example about 2% or about 1% w/w of the pharmaceutical composition. In particular formulations, for example when formulated as a hydrogel or an ointment, the PS may be at a concentration of 5% w/w of the pharmaceutical composition.

A single application to both hands (i.e., the gloves) may require less than about 5 ml of the pharmaceutical composition, for example about 3 ml of the pharmaceutical composition (i.e., about 1.5 ml of the pharmaceutical composition per hand). A single application to both feet (i.e., the stockings) may require less than about 6 ml of the pharmaceutical composition, for example about 4 ml of the pharmaceutical composition (i.e., about 2 ml of the pharmaceutical composition per foot).

The pharmaceutical composition comprising PS may alternatively be formulated for any other form of administration suitable for treating and/or preventing neuropathic pain associated with CIPN. For example, the composition may be formulated for transdermal administration or injection, for example subcutaneous injection.

Dosing Regimens

The appropriate dosage regimen for PS for treating and/or preventing CIPN will depend on such variables as the type and extent of progression of the pain (e.g., as determined by the "Pain Ladder" guideline from the World Health Organization), the severity of the pain (e.g., acute, subacute, or chronic), the age, weight, and general condition of the particular patient, formulation of the excipient, the route of administration, and the judgment of the attending clinician.

For topical administration, the PS can be administered to cover the one or more affected areas, for example the upper and lower limbs of the subject. In some embodiments, about 0.01 to about 5 g of the PS may be administered to the affected area. With respect to the size of the affected area, the PS may be administered at about 0.005-0.25 g/10 $cm^2$ of affected area. Therefore, the PS may be administered at about 0.005 g/10 $cm^2$, 0.01 g/10 $cm^2$, 0.05 g/10 $cm^2$, 0.1 g/10 $cm^2$, 0.15 g/10 $cm^2$, 0.2 g/10 $cm^2$ or 0.25 g/10 $cm^2$ of affected area.

The PS for use in topical administration in some instances may be applied and then removed from the affected area (e.g., by washing off) before reapplication. In some instances the PS is washed off after a certain period of time. Alternatively, as the analgesic effect may reduce over time and reapplication may be necessary, in some instances the PS is not washed off and instead PS is simply reapplied to the affected area after passing of the appropriate dosing period. For example, PS may be applied to the affected area and left on the affected area (before removal or reapplication) for between about 0.5 hours and about 5 hours. Accordingly, PS may be applied topically and left on the affected area (before removal or reapplication) for about 0.5 hours, for about 1 hour, for about 2 hours, for about 3 hours, for about 4 hours, or for about 5 hours.

As neuropathic pain associated with CIPN is chronic, it is necessary to repeat topical administration of PS. Accordingly, the PS may be applied topically 1 to 4 times a day. Therefore, the PS may be applied once a day, twice a day, three times a day, or four times a day. With particular formulations of PS, for example a hydrogel or ointment with a PS concentration of about 5% w/w of the pharmaceutical composition, the formulation may be applied topically three times a day. In more severe cases, a further application of PS may be applied about 0.5 hours after each application.

The PS may have a long-lasting analgesic effect and thus can be administered less frequently. For example, the PS can be administered topically less than once a day, for example once every other day. Indeed, for those patients experiencing long-term analgesia with a single administration, the PS may be administered topically less than once a week, for example once a fortnight.

For topical administration of some pharmaceutical compositions, it is useful to cover the affected area, for example with a dressing (e.g., a plastic wrap or film), after the pharmaceutical composition has been applied, for example to ensure appropriate amount of the composition can be applied for an appropriate time. Therefore, after topical application of the PS, the affected area may be dressed.

In some embodiments, the PS may be administered topically in the form of a patch, for example a medicated plaster. The use of a patch may allow the dosing interval and/or dosing frequency to be reduced, for example due to the patch ensuring controlled release of the PS. Accordingly, the patch may be applied to the affected area once a day, less than twice a day, less than three times a day, or less than four times a day.

The administration of the PS may continue as long as necessary. For example, the PS may be administered for more than 1, 2, 3, 4, 5, 6, 7, 14, 28, 56, or 84 days. As noted above, the PS can be administered chronically on an ongoing basis for the treatment of chronic effects, for example for at least 3 months. Accordingly, in some cases, continuous dosing is achieved and maintained as long as necessary. The PS may be administered intermittently according to the recurrence of the neuropathic pain and/or associated sensory symptoms.

The PS can be used for the treatment and/or prevention of CIPN in mammals. For example the subject may be a human.

As noted above, PS can be formulated into an appropriate pharmaceutical composition for administering to subjects with CIPN. Accordingly, the PS may be administered according to the dosing regimens above in an appropriate pharmaceutical composition.

A person having ordinary skill in the art understands that, in certain embodiments, dosages of such compounds may be adjusted depending upon the mammal to be treated. For example, the treatment of mice is described herein and such dosages may or may not be revised upon the administration of PS to a human. However, a person having ordinary skill in the art may, if necessary, convert the dosages provided herein as set forth in Guidance for Industry: Estimating the Maximum Safe Starting Dose in Initial Clinical Trials for Therapeutics in Adult Healthy Volunteers, U.S. Department of Health and Human Services, Food and Drug Administration, Center for Drug Evaluation and Research (CDER), July 2005. A human equivalent dose (HED) may be determined from an animal dose, the animal dose may be multiplied by the following conversion factors, to provide units in mg/kg: mouse=0.08, hamster=0.13, rat=0.16, ferret=0.19, guinea pig=0.22, rabbit=0.32, dog=0.54, monkey=0.32, marmoset=0.16, squirrel monkey=0.19, baboon=0.54, micropig=0.73, and mini-pig=0.95.

Pharmaceutically Acceptable Forms of PS

The pharmaceutical composition comprising PS can contain a pharmaceutically acceptable form of PS. The pharmaceutically acceptable form may be a solvate, derivative, and/or prodrug.

Solvates

As used herein, the term "solvate" refers to a compound that further includes a stoichiometric or non-stoichiometric amount of solvent bound by non-covalent intermolecular forces. Where the solvent is water, the solvate is a hydrate. The pharmaceutically acceptable form of PS may include a solvate of PS, for example a solvate of PS-I and/or PS-II. In some embodiments, the solvate includes at least 1 molecule of solvent. In some embodiments, the solvate includes less than 1 molecule of solvent. In some embodiments, the solvate is a hydrate.

Isotopes

The pharmaceutically acceptable form of PS may include an isotopically labelled derivative of PS-I. The pharmaceutically acceptable form of PS may include an isotopically labelled derivative of PS-II. An isotopically labelled derivative is a compound that is identical to PS, except that one or more atoms are replaced by an atom having an atomic mass or mass number different from the atomic mass or mass number usually found in nature. In some embodiments, the isotopically labelled derivative of PS includes one or more isotopes of hydrogen, carbon, oxygen, phosphorus, and fluorine. In some embodiments, the isotopically labelled derivative of PS includes one or more isotopes of $^2H$, $^3H$, $^{13}C$, $^{14}C$, $^{18}O$, $^{17}O$, $^{31}P$, $^{32}P$, $^{35}S$, and $^{18}F$, respectively. In some embodiments, the isotopically labelled derivative of PS includes one or more isotopes of $^2H$ (e.g., deuterium). In some embodiments, the isotopically labelled derivative of PS includes one or more isotopes of $^3H$ (e.g., tritium). In some embodiments, the isotopically labelled derivative of PS includes one or more isotopes of $^{14}C$.

Derivatives and Prodrugs

The pharmaceutically acceptable form of PS may include a derivative of PS-I. The pharmaceutically acceptable form of PS may include a derivative of PS-II. In some embodiments, the derivative of PS (e.g., PS-I or PS-II) is a metabolite. In other embodiments, the pharmaceutically acceptable form of PS is a prodrug of PS, for example a prodrug of PS-I or a prodrug of PS-II.

A sulfone group can be structurally expressed as: R—S(=O)$_2$—R'. In some embodiments, the derivative of PS is a sulfone form of PS.

PS contains an organophosphate functional group. An organophosphate functional group can be structurally expressed as O=P(OR)$_3$, O=P(OR)$_2$(OR'), or O=P(OR)(OR')(OR''). For example, O=P(OR)$_2$(OR') can represent PS if R=CH$_2$CH$_3$ and R'=the remainder of the molecule is as per PS in formula I or II (e.g., PS-I, PS-II, or a derivative thereof).

In some embodiments, the derivative of PS is PS wherein one of the ethoxy (e.g. —OCH$_2$CH$_3$) groups is an OH group, or a pharmaceutically acceptable salt thereof. In some embodiments, the derivative of PS is PS wherein both ethoxy (e.g. —OCH$_2$CH$_3$) groups are OH groups, or a pharmaceutically acceptable salt thereof.

The activity of PS demonstrated herein would be shared by pharmaceutically acceptable forms thereof. Therefore, the present invention provides pharmaceutically acceptable forms of PS for use in the methods of the invention.

While preferred embodiments of the invention are shown and described herein, such embodiments are provided by way of example only and are not intended to otherwise limit the scope of the invention. Various alternatives to the described embodiments of the invention may be employed in practicing the invention.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1 The Effect of PS in Preventing Neuropathic Pain in a Mouse Model of CIPN CIPN was induced in a population of mice using paclitaxel. This is a well-established model for CIPN (Hidaka et al. (2012) European Journal of Pain 13(1): 22-27) and is relevant for human therapy, not least because paclitaxel is widely used in cancer chemotherapy for the treatment of solid tumours, including breast, ovarian and lung cancer. The experiments herein demonstrate the efficacy of PS in prevention of pain associated with CIPN.

Methods

In order to establish CIPN, paclitaxel is administered at 10 mg/kg intraperitoneally into C57/BL mice. The paclitaxel was administered into all study groups (except the naïve group) once a day for 5 days. This dosing regimen of paclitaxel produces pain associated with CIPN with time courses that are similar to those of pain after paclitaxel administration in cancer patients.

PS (as an 8% hydrogel) or vehicle control were administered topically to both hind paws of the mice 3 times a day for 7 days. The first doses were administered 2 days prior to the first administration of paclitaxel.

The study groups were as follows:
1. Group 1: naïve mice (i.e. no paclitaxel)
2. Group 2: paclitaxel only (n=6)
3. Group 3: paclitaxel plus vehicle (n=7)
4. Group 4: paclitaxel plus PS (n=7)

In order to determine the outcome of the treatment, pain threshold responses were measured using the well-established method of von Frey filaments. In particular, a simplified up-down method for estimating paw withdrawal threshold (PWT) using von Frey filaments was used (as described in Bonin et al., Molecular Pain (2014); 10(26):1-10)). The results of the PWT test are expressed as force applied (gm). The PWT test was performed at baseline (i.e., 4 days prior to paclitaxel administration (day—4)) and then one day following the final treatment with PS or vehicle (i.e., day 6 after the first administration of paclitaxel).

FIG. 1 provides an outline of the study.

Results

Figure 2:
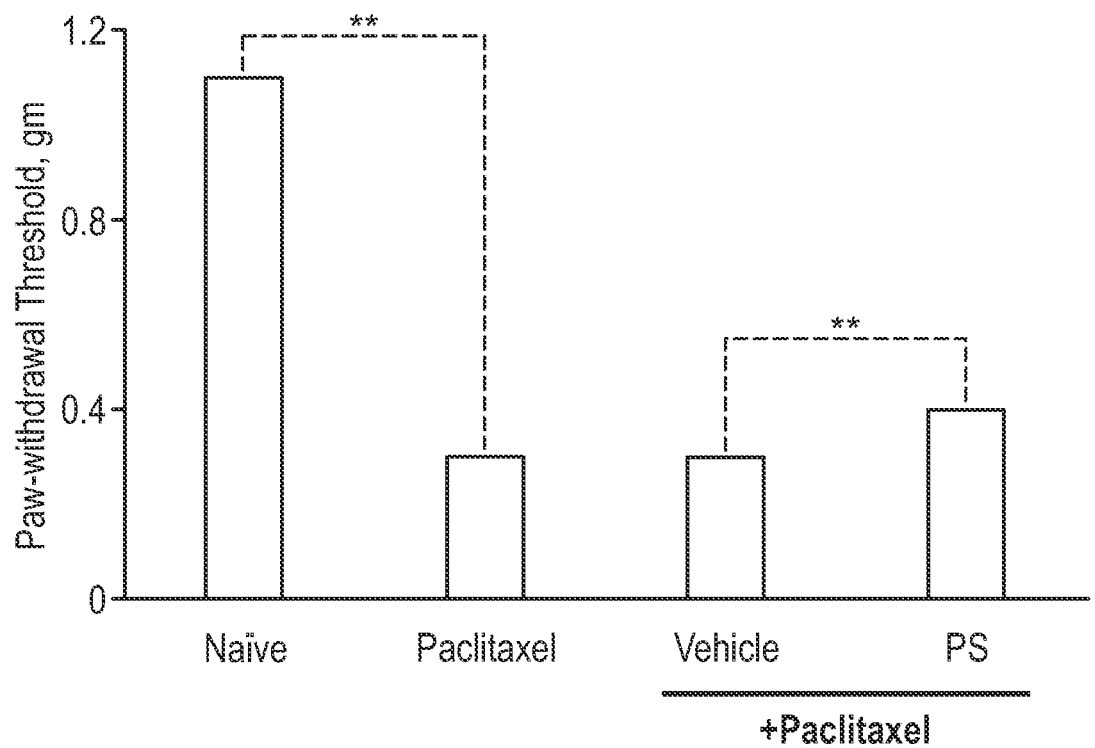
FIG. 2—effect of PS on preventing neuropathic pain associated with CIPN, compared to vehicle.

As displayed in FIG. 2, the administration of paclitaxel resulted in a significant decrease in PWT (p<0.01 vs. naïve mice), as expected. Therefore, the model established pain associated with chemotherapy. The additional administration of vehicle has no significant effect on the PWT compared to treatment with paclitaxel only, while administration of PS achieved a significant increase in PWT compared to vehicle (p<0.01 vs vehicle). The values, corresponding to FIG. 2, are provided in Table 1.

TABLE 1

PWT in the 4 study groups

| Groups | PWT, gm Mean ± SEM | P values |
|---|---|---|
| Naïve | 1.1 ± 0.01 | |
| Paclitaxel only | 0.3 ± 0.01 | *p < 0.01 vs naïve |
| Paclitaxel + vehicle | 0.3 ± 0.01 | NS vs paclitaxel only |
| Paclitaxel + PS | 0.4 ± 0.01 | *p < 0.01 vs vehicle |

Conclusions

The topical administration of PS significantly increased the PWT in mice displaying neuropathic pain caused by paclitaxel (i.e., CIPN). Therefore, PS is preventing the pain associated with CIPN.

NSAIDs, such as loxoprofen sodium, have been shown to be ineffective in reducing pain signalling in this CIPN model (Hidaka et al. (2009) *European Journal of Pain* 13: 22-27). This is in line with the observations in Moore et al. (2015) *Cochrane Database of Systematic Reviews* 10: 1-25, in which NSAIDs are shown to have no therapeutic efficacy in peripheral neuropathic pain.

Contrary to the observations with typical NSAIDs, PS is clearly demonstrating a pain-relieving effect in CIPN. Indeed, this striking activity of PS, in a specific animal model of CIPN, supports observations that unlike typical NSAIDs, PS can effectively prevent neuropathic pain associated with chemotherapy induced neuropathy.

Example 2 the Effect of PS in Treating Neuropathic Pain in a Mouse Model of CIPN Methods CIPN was established by administration of 10 mg/kg paclitaxel intraperitoneally into C57/BL mice. The paclitaxel was administered into all study groups once a day for 3 days. The results of FIG. 2 demonstrate that paclitaxel causes a significant decrease in PWT compared to naïve mice.

PS (as an 8% hydrogel) or vehicle control were administered topically to both hind paws of the mice 3 times a day for 10 days. The first doses were administered 2 days after the last administration of paclitaxel.

The study groups were as follows:
1. Group 1: paclitaxel only (n=9)
2. Group 2: paclitaxel plus vehicle (n=10)
3. Group 3: paclitaxel plus PS (n=10)

In order to determine the outcome of the treatment, pain threshold responses were measured using the well-established method of von Frey filaments in line with that performed in Example 1. The PWT test was performed at baseline (i.e., 4 days after the first dose of paclitaxel administration (day-1)) and then on the final day of treatment with PS or vehicle (i.e., day 10, about 30 minutes after the last application. The data is expressed as percent change from the respective baseline value.

Figure 3:
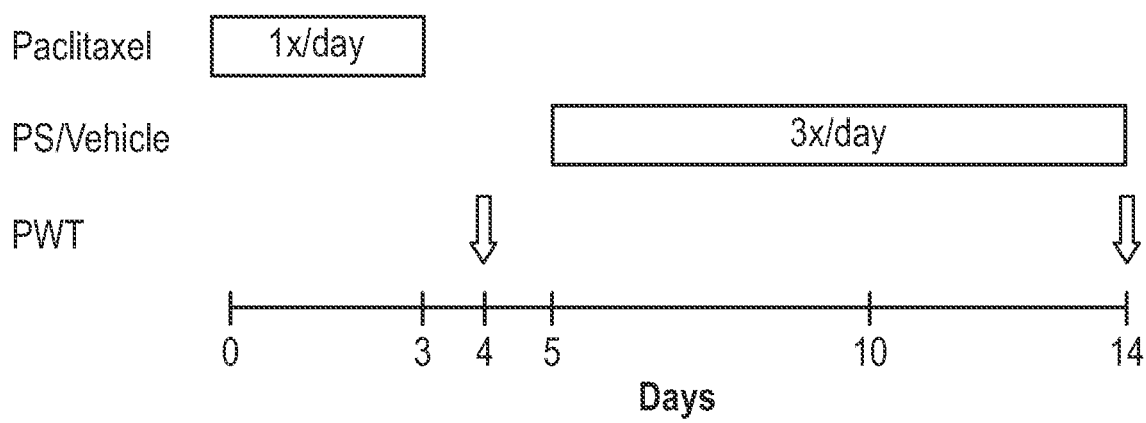
FIG. 3—schematic outline of the neuropathic pain associated with CIPN treatment study.

FIG. 3 provides an outline of the study.

Results

Figure 4:
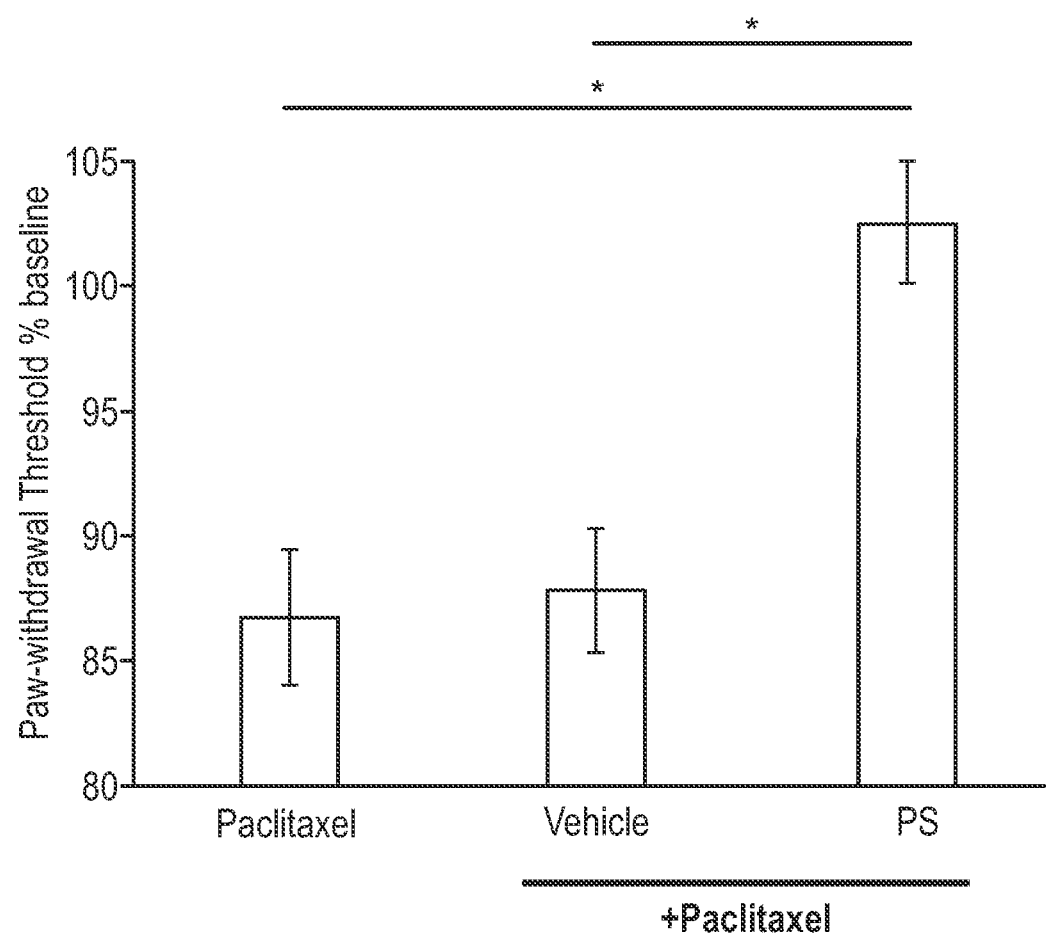
FIG. 4—effect of PS on treating neuropathic pain associated with CIPN.

As displayed in FIG. 4, the administration of vehicle in the paclitaxel background has limited effect on the PWT compared to treatment with paclitaxel only, while administration of PS achieved a significant increase in PWT compared to vehicle and paclitaxel alone. The values, corresponding to FIG. 4, are provided in Table 2.

TABLE 2

PWT in the 3 study groups

| Groups | PWT, % baseline Mean ± SEM | P values |
|---|---|---|
| Paclitaxel only | 86.75 ± 5.42 | |
| Paclitaxel + vehicle | 87.77 ± 5.02 | |
| Paclitaxel + PS | 102.55 ± 4.92 | *p < 0.04 vs vehicle *p < 0.03 vs paclitaxel alone |

Conclusions

The topical administration of PS significantly increased the PWT in mice with established neuropathic pain caused by paclitaxel (i.e., CIPN). Therefore, PS treats the pain associated with CIPN.

Consistent with the observations in Example 1 and contrary to the observations with typical NSAIDs, PS demonstrates a pain-relieving effect in a treatment model of pain associated with CIPN. This striking activity of PS, in a specific animal model of CIPN, supports observations that unlike typical NSAIDs, PS can effectively treat neuropathic pain associated with chemotherapy induced neuropathy.

Example 3 PS Effectively Treats Neuropathic Pain Associated with CIPN Caused by Multiple Different Chemotherapeutics Methods Animals Adult male C57BL/6J mice, 8 weeks of age at the beginning of the experiments and weighing 20-30 g, were purchased from The Jackson Laboratory (Bar Harbor, ME). Mice were housed in an AAALAC-accredited facility in groups of four. Food and water were available ad libitum. The mice in each cage were randomly allocated to treatment groups. All studies were conducted by experimenters blinded to the identity of the treatment groups. Experiments were performed during the light cycle (7:00 am to 7:00 pm) and animals were euthanized with $CO_2$ asphyxiation. Studies were approved by the relevant Institutional Animal Care and Use Committee and followed the National Institutes of Health Guidelines for the Care and Use of Laboratory Animals. Animal studies are reported in compliance with the ARRIVE guidelines.

Phosphosulindac

PS was formulated as an 8% hydrogel ointment for topical administration.

Induction of CIPN

CIPN was induced in mice with three different chemotherapeutic compounds using established protocols (Carozzi et al., Exp Neurol (2010); 226:301-309; Currie et al., PLOS Biol (2019); 17:e3000243; Eldridge et al., Toxicol Pathol (2020); 48:190-201). Each of the three chemotherapeutic compounds were prepared and dosed as follows:

Paclitaxel: paclitaxel (purchased from MilliporeSigma (St. Louis, MO)) was dissolved in a mixture of 1 volume ethanol/1 volume Cremophor EL (EMD Millipore Corp, Burlington, MA)/18 volumes distilled water. Paclitaxel was administered as four intraperitoneal injections of 8 mg/kg paclitaxel (in a volume of 1 ml/100 g body weight) every other day, resulting in a cumulative dose of 32 mg/kg.

Oxaliplatin: Oxaliplatin was dissolved in $ddH_2O$. Oxaliplatin 3 mg/kg was injected intraperitoneally daily for 5 days, followed by 5 days of no treatment, which was followed by another 5-day period of daily oxaliplatin intraperitoneal injections as previously for a total of ten injections leading to a cumulative dose of 30 mg/kg. All injections were administered intraperitoneally in a volume of 1 ml/100 g body weight.

Vincristine: Vincristine was dissolved in PBS. Two intraperitoneal injections of vincristine 1.5 mg/kg were made within one week for a total cumulative dose of 3 mg/kg. All injections were administered intraperitoneally in a volume of 1 ml/100 g body weight.

Figure 5:
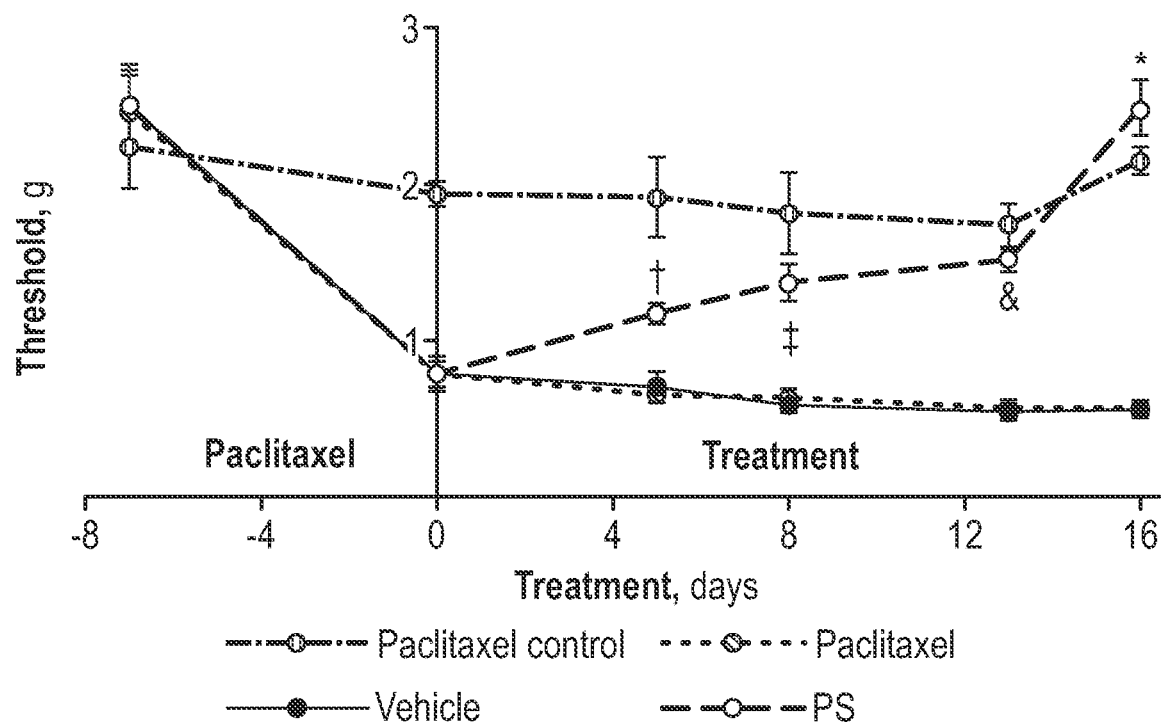
FIG. 5—effect of PS on treating neuropathic pain associated with paclitaxel-induced CIPN. The effect of PS compared to its vehicle control was significant from day 5 and increased thereafter ($^\dagger$, $p<0.002$, $^\ddagger$, $p=4.9\times10^{-5}$, $^\&$, $p=1.7\times10^{-7}$, *, $p=2.2\times10^{-7}$).
Figure 6:
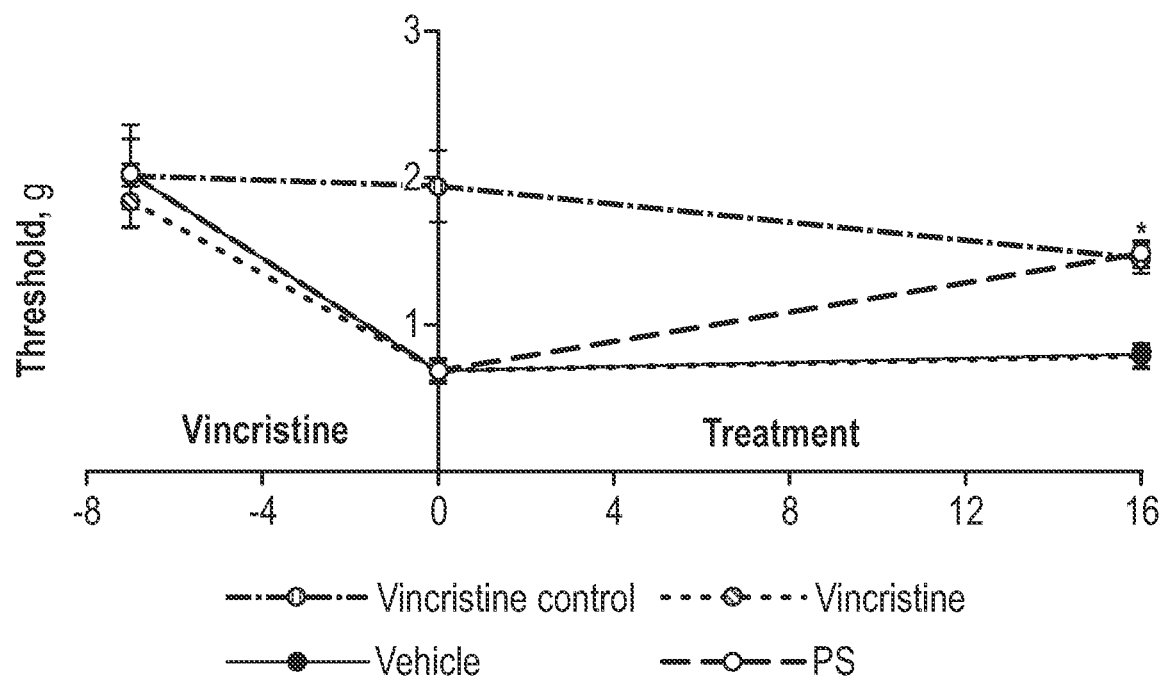
FIG. 6—effect of PS on treating neuropathic pain associated with vincristine-induced CIPN. The effect of PS compared to its vehicle control was significant on day 16 (* $p=8.6\times10^{-6}$).
Figure 7:
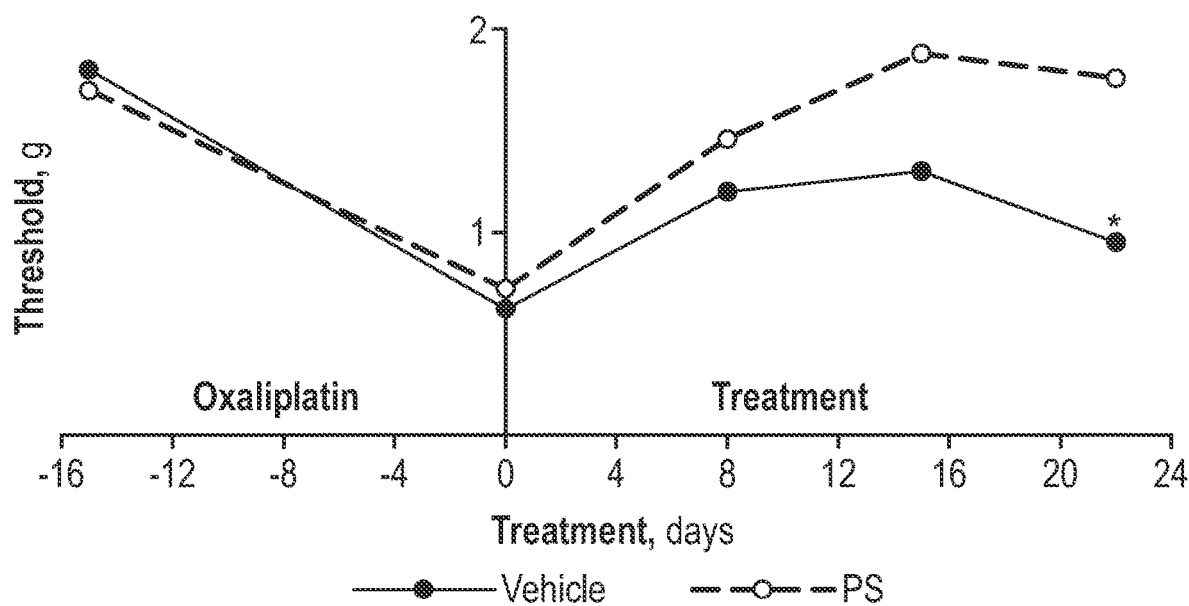
FIG. 7—effect of PS on treating neuropathic pain associated with oxaliplatin-induced CIPN. The effect of PS compared to its vehicle control was significant on day 22 (* $p=0.004$).

Protocol for the Treatment of Established Neuropathic Pain Associated with CIPN with PS Once CIPN was established documented by reduced mechanical allodynia threshold, PS 8% or placebo hydrogel ointment was applied three times daily to the hind paws of the mice for the duration of the assessment period (see FIGS. 5-7). Mechanical allodynia was measured at the time points recorded in the figures.

Assessment of Mechanical Allodynia (Von Frey Test)

Mechanical allodynia thresholds were determined using von Frey filaments according to an established method (Chaplan et al., J Neurosci Methods (1994); 53:55-63; Bagdas et al., Biochem Pharmacol (2015); 97:590-600). Briefly, mice were placed in a quiet room for 30 min and then were put in a Plexiglas cage with mesh metal flooring and allowed to acclimatise for 30 min before testing. A series of calibrated von Frey filaments (Stoelting, Wood Dale, IL) with incremental stiffness were applied perpendicularly to the paw with sufficient force to cause slight bending and held 2-3 s. This process was repeated at each level of stiffness 5 times, a few seconds apart. Paw withdrawn, licking or shaking were considered positive responses. The mechanical threshold, expressed as g, indicates the force of the von Frey filament to which the animal reacted.

Statistical Analysis

Results are expressed as mean±SEM. PK parameters were calculated by Microsoft Excel and PKSolver. Non-compartmental analyses were employed. Analysis of variance (ANOVA) tests were conducted and followed by the Bonferroni post hoc test. Differences were determined to be significant at $P<0.05$.

Results

The effect of PS in mice with neuropathic pain associated with three different chemotherapeutic compounds was assessed. This reflects the clinical situation considered in Example 2 already, in which patients present with neuropathic pain after their chemotherapy is initiated or completed.

As shown in FIGS. 5-7, each of the three anticancer drugs studied induced significant neuropathic pain, evidenced by changes in mechanical allodynia. Topical treatment with PS 8% ointment 3×/day was started after the neuropathic pain was established.

Each of the different chemotherapeutic compounds are discussed separately below.

Paclitaxel (see FIG. 5):

At baseline, all four study groups of mice had essentially identical allodynia scores (range 2.24±0.26 g to 2.49±0.24 g; mean±SEM for this and all subsequent values). Paclitaxel administered to three study groups over 12 days greatly reduced (~85%) their mechanical allodynia scores indicative of neuropathic pain associated with CIPN. In contrast, the control group (non-paclitaxel, non-PS) showed a minor, statistically non-significant variation in allodynia scores throughout the entire study period.

When PS was applied to the paws of mice with paclitaxel-induced neuropathic pain, their allodynia score showed progressive improvement from its lowest point at the initiation of treatment returning it to its baseline on day 16 (day 0=0.79±0.08 g vs. day 16=2.49±0.18 g; $p=1.6\times10^{-6}$). In contrast, the vehicle-treated group showed a mild deterioration of the allodynia score (day 0=0.79±0.11 g vs. day 16=0.56±0.05 g; p=NS). The paclitaxel only treated group showed changes in the allodynia score similar to those of the vehicle group (day 0=0.78±0.08 g vs. day 16=0.57±0.05 g; p=NS).

The difference between the PS-treated group and its vehicle control first became statistically significant on day 5 (PS=1.17±0.07 g, vehicle=0.7±0.07 g; p=0.002), with their difference increasing thereafter and becoming maximal on day 16 (PS=2.49±0.18 g, vehicle=0.56±0.05 g; $p=2.1\times10^{-7}$).

Vincristine (See FIG. 6):

PS improved the mechanical allodynia induced by the commonly used vincristine. In the three groups it was administered, vincristine reduced the mechanical allodynia score by 61%-65% (day-7 scores range between 1.8±0.18 g and 2.0±0.24 g vs. day 0=0.7±0.07 g for all; $p=3.2\times10^{-6}$). In contrast, the control group that received the solvent alone showed no change in allodynia during these 7 days. PS treatment of mice with vincristine-induced neuropathic pain for 16 days markedly improved allodynia scores (114% increase compared to day 0; $p=1.3\times10^{-6}$), with their score being identical to that of the control group (no vincristine).

The difference between the PS-treated group and its vehicle control was statistically significant on day 16 (PS=1.5±0.09 g, vehicle=0.8±0.09 g; $p=8.6\times10^{-6}$). There was no appreciable change in allodynia scores during the same period of time in the vehicle and vincristine alone groups (0.7±0.07 g vs. 0.8±0.09 g for both).

Oxaliplatin (See FIG. 7):

As expected, during oxaliplatin administration, the allodynia score was reduced by 65% and 56% in the two study groups at day 0 respectively.

PS treatment restored allodynia scores to the day-15 baseline (1.8±0.09 g vs. 1.76±0.13 g) whereas the vehicle group continued to show suppressed allodynia scores, being 47% lower on day 22 compared to day-15. The difference between the PS- and vehicle-treated groups became statistically significant on day 22 (p=0.004).

Safety of PS

During all the studies, no topical or systemic side effects of PS ointment were observed when applied thrice daily to the hind paws of mice for up to 22 days. This finding is in keeping with the known safety profile of PS.

Conclusions

The topical administration of PS significantly improves the mechanical allodynia score compared to that induced by three different chemotherapeutic compounds. Therefore, PS treats the neuropathic pain induced by a range of different chemotherapies.

Consistent with the observations in Example 2, PS demonstrates a pain-relieving effect in a treatment model of neuropathic pain associated with CIPN caused by chemotherapeutic compounds from different therapeutic classes.

Example 4 PS Effectively Prevents Neuropathic Pain Associated with CIPN Caused by Paclitaxel Similar to the experiments discussed in Example 1, the ability of PS to prevent neuropathic pain associated with paclitaxel chemotherapy was assessed. This experiment uses a different paclitaxel dosing regimen compared to Example 1. The corresponding clinical situation, as in Example 1, is that in which the neuropathic pain therapy is administered prior to, or concomitantly with the chemotherapy. Mechanical allodynia was used as an end point for assessing the effect on neuropathic pain associated with CIPN.

Methods

The methods with respect to animals, induction of CIPN (with paclitaxel), assessment of mechanical allodynia and statistical analysis correspond to those outlined in Example 3.

Regarding the prevention of neuropathic pain associated with CIPN, administration of PS 8% or vehicle to the hind paws of mice as above started two days before initiating the administration of paclitaxel compounds as explained for Example 3. Mechanical allodynia was measured before the administration of PS and on day 10 after initiation of PS treatment.

Results

Figure 8:
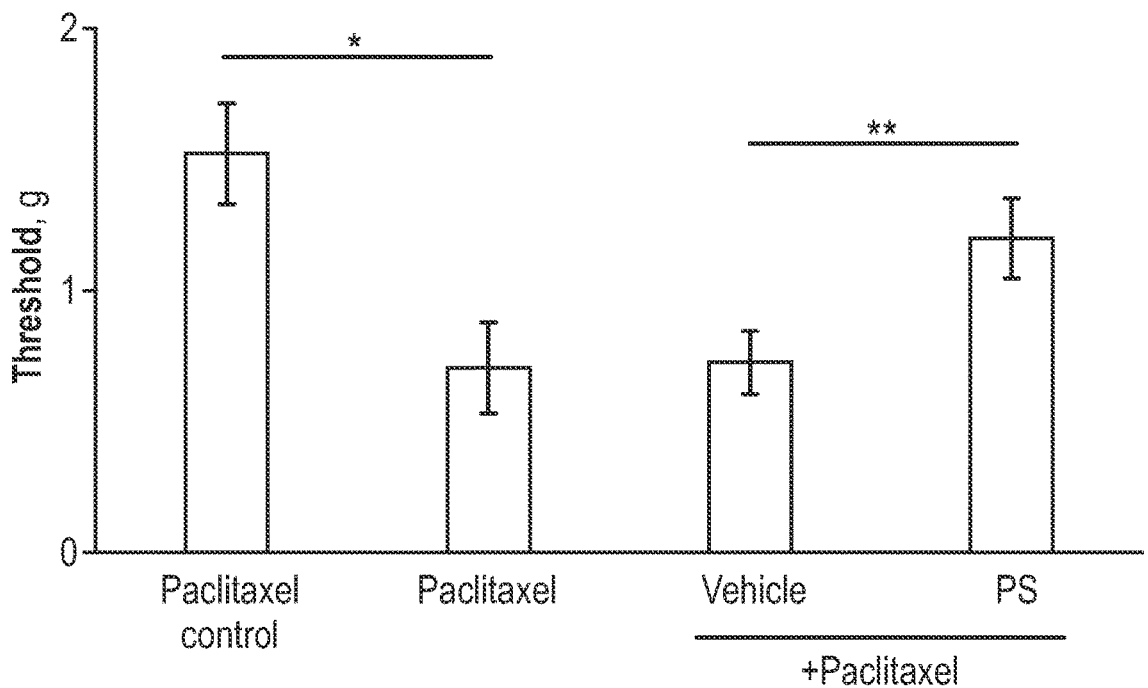
FIG. 8—effect of PS on preventing neuropathic pain associated with paclitaxel-induced CIPN. The effect of PS compared to its vehicle control was significant (*, $p=3.0\times10^{-8}$, **, $p=2.3\times10^{-6}$).

In the prevention study depicted in FIG. 8, three of the four study groups of mice were treated with paclitaxel (one injection every other day for a total of four) while the fourth group received the solvent alone, serving as control. Two of the paclitaxel-treated groups were started on topical treatment with PS ointment or vehicle (ointment alone) 2 days prior to the first dose of paclitaxel.

At the end of the study (day 10), the mechanical allodynia score of the paclitaxel group was 53% lower than its control ($0.7 \pm 0.17$ g vs. $1.5 \pm 0.19$ g; $p=3 \times 10^{-8}$). The allodynia score of the vehicle-treated group was identical to the paclitaxel only group ($0.7 \pm 0.12$ vs. $0.7 \pm 0.17$). However, the allodynia score of the pre-treated PS group was significantly increased compared to the vehicle group ($1.2 \pm 0.15$ g vs. $0.7 \pm 0.12$ g; $p=2.3 \times 10^{-6}$), bringing it close to that of the paclitaxel (solvent alone) control ($1.5 \pm 0.19$ g).

With respect to safety, no topical or systemic side effects of PS ointment were observed.

Conclusions

Similar to the conclusions for Example 1, the topical administration of PS significantly increases the paw-with-drawal threshold compared to its vehicle. Therefore, PS prevents development of neuropathic pain caused by administration of paclitaxel. The study compliments the findings of Example 1, demonstrating that the effect is observed irrespective of the administration regimen used for paclitaxel.

Example 5 Pharmacokinetics and Biodistribution of PS

Given the ability of PS to treat and prevent neuropathic pain associated with CIPN, the site of action of PS was investigated. Despite being topically administered, PS was found to traverse within nerves from the periphery towards the spinal cord.

Methods

PS 8% ointment was applied topically to each hind paw (50 µl per paw) with gentle rubbing. At 0.5, 1, 3, 5, 12, 18, and 24 h, mice (n=4-5 mice/time point) were euthanized with $CO_2$ inhalation. Blood was drawn immediately after death. Tissues, including paw skin, paw muscle, leg muscle, the sciatic nerve and lumbar DRG bilaterally were dissected quickly, immediately frozen in liquid nitrogen and stored at $-80°$ C. until analyzed.

In a separate experiment we studied 8 mice with paclitaxel-induced PN treated with PS 8% ointment 3x/d for 2 wks. Mice were euthanized as above 30 minutes after the last dose of PS. From these mice we harvested both sciatic nerves dividing each into proximal and distal halves, and combined the corresponding halves of every two animals for assay of drug levels.

As previously described (Wen et al., Int J Pharm (2019); 557:273-279), each plasma sample was mixed with double volume of acetonitrile and centrifuged at 13,200 rpm for 15 min. Tissue samples were weighed, $ddH_2O$ (100-300 µL, depending on tissue weight) was added and they were homogenized. Following addition of acetonitrile (twice the volume of the homogenate), the mixture was sonicated for 10 min, centrifuged at 13,200 rpm for 15 min, and analyzed by HPLC, as reported (Wen et al., 2019). The limit of quantitation is 0.1 µM for PS and 0.05 µM for sulindac, sulindac sulfone, sulindac sulfide and their glucuronidated derivatives.

Results

Figure 9:
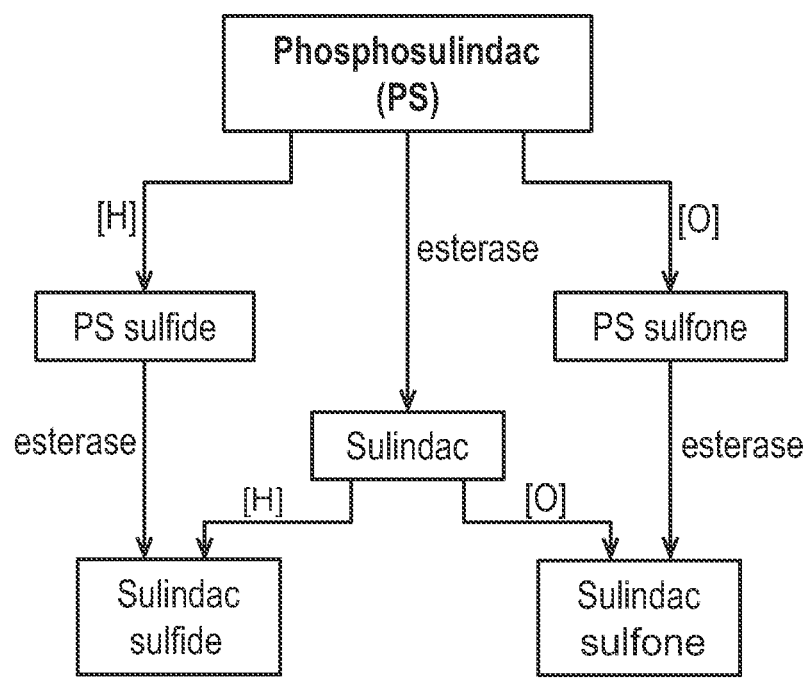
FIG. 9—schematic outline of the metabolism of PS.

PS can be rapidly metabolized into several metabolites both in vitro and in vivo that include PS sulfide, PS sulfone, sulindac, sulindac sulfide and sulindac sulfone (FIG. 9). Glucuronides of sulindac and its metabolites, mainly forming in the liver, have also been identified. Since the metabolism and PK/biodistribution of PS vary depending on its route of administration, we studied both in normal mice in which PS was administered topically to their hind paws, with particular attention to the sciatic nerve and the dorsal root ganglia (DRG) that are affected in CIPN (Colvin, Pain (2019); 160 Suppl 1:S1-S10).

Figure 10:
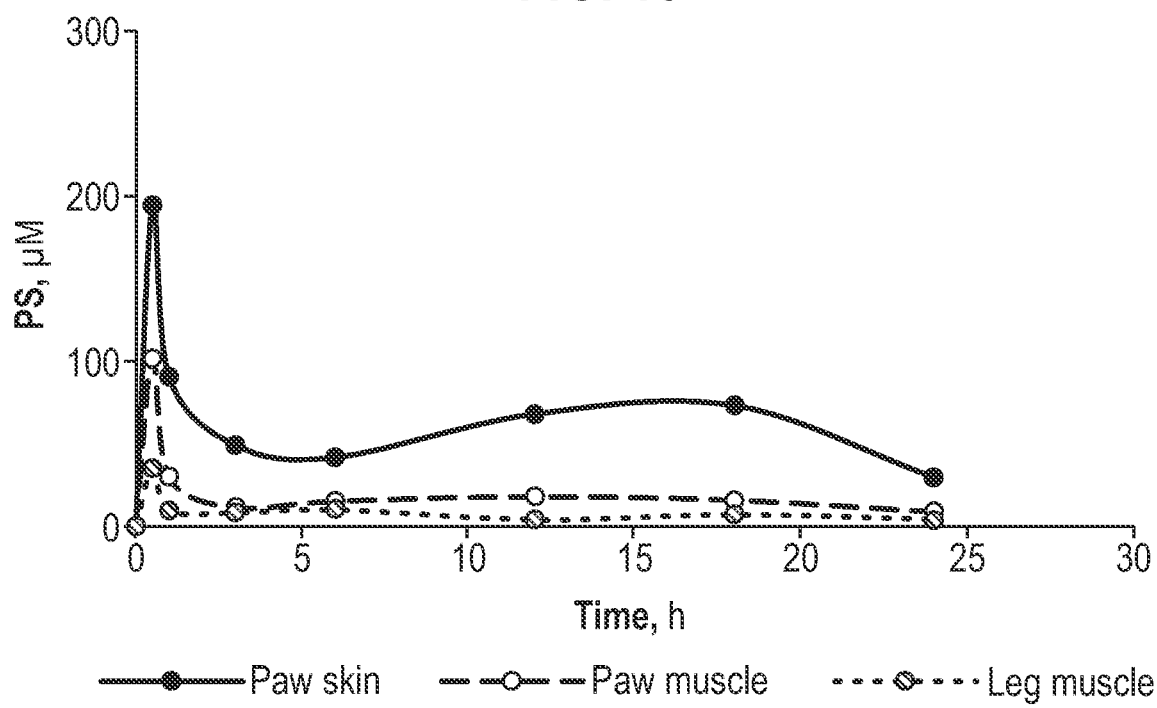
FIG. 10—biodistribution of PS in different tissues upon topical administration. SN=sciatic nerve. DRG=dorsal root ganglia.
Figure 10:
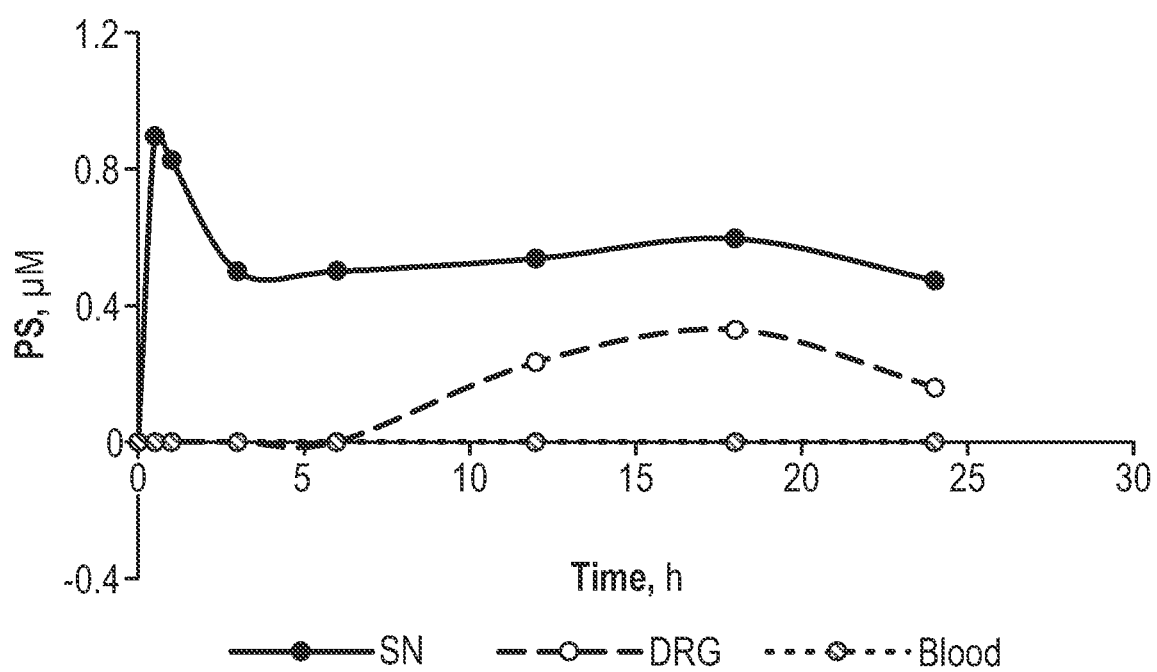

As shown in FIG. 10 and Table 3, PS was detected in paw skin, the site of its application, the muscles underneath the skin, leg muscles, the sciatic nerve, and DRG. As expected (Xie et al., Br J Pharmacol (2012a); 165:2152-2166), no PS was detected in the systemic circulation.

The concentration of PS progressively decreased from the skin to its most distant DRG, evidenced by the respective values of both $C_{max}$ (from $194.7 \pm 5.3$ µM to $0.3 \pm 0.1$ µM) and $AUC_{0-24\,h}$ (from 1,609.8 µM·h to 4.5 µM·h). The $T_{max}$ of PS was the same in all tissues (0.5 h) with the exception of DRG that showed a prolonged $T_{max}$ (18 h), reflecting perhaps the manner in which PS reaches it, as discussed below. Another interesting feature is the difference in $t_{1/2}$ of the skin and the muscles, which is within a relatively narrow range (11.4-20.6 h), in contrast to the much-prolonged value of 57.4 h in the sciatic nerve and the likely even more prolonged value in DRG, which could not be determined with reasonable accuracy.

These differences indicate differential metabolic capacity regarding PS between the nerve and skin and muscles.

TABLE 3

PK parameters of PS in mouse tissue and peripheral blood of normal mice

| Tissue | $C_{max}$, µM mean ± SEM | $T_{max}$, h | $T_{1/2}$, h | $AUC_{0-24\,h}$, µM · h |
|---|---|---|---|---|
| Paw skin | 194.7 ± 5.3 | 0.5 | 16.1 | 1,609.8 |
| Paw muscle | 101.7 ± 4.6 | 0.5 | 11.4 | 411.2 |
| Leg muscle | 35.0 ± 3.6 | 0.5 | 20.6 | 171.6 |
| SN | 0.9 ± 0.1 | 0.5 | 57.4 | 12.0 |
| DRG | 0.3 ± 0.1 | 18 | * | 4.5 |
| Blood | ** | ** | ** | ** |

\* cannot be determined.
\*\* cannot be calculated because intact PS was undetectable. N = 4-5 mice/time point.

Figure 11:
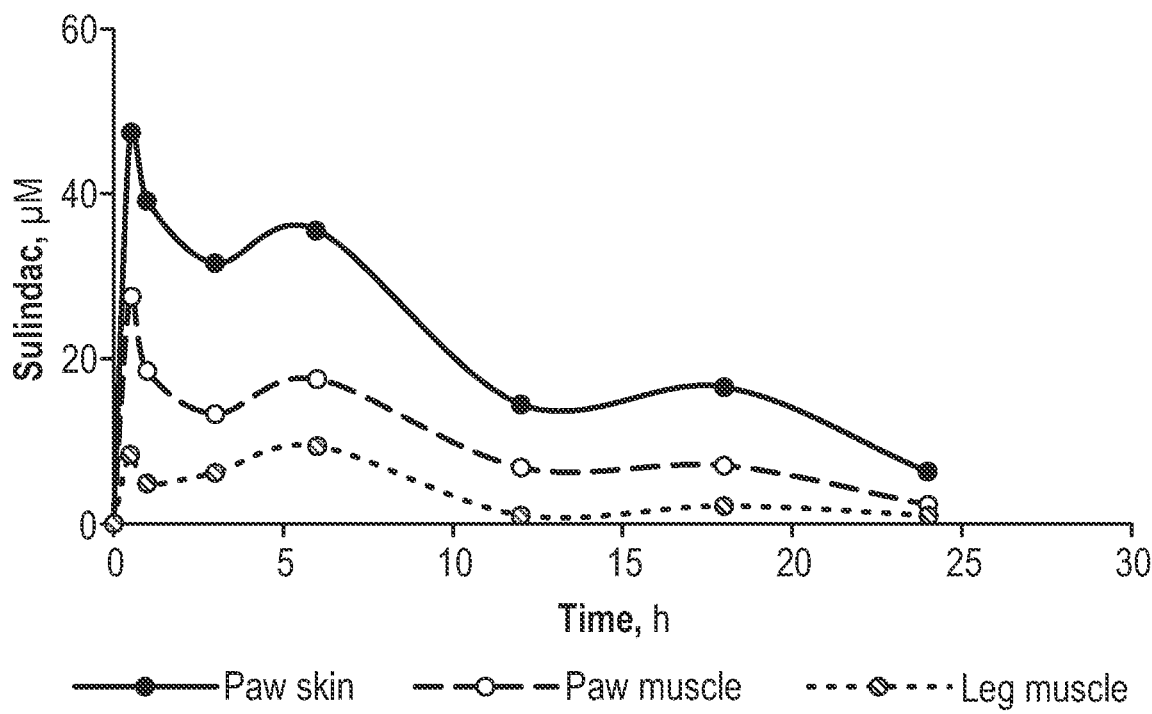
FIG. 11—biodistribution of the metabolites of PS in different tissues upon topical administration of PS. SN=sciatic nerve. DRG=dorsal root ganglia.
Figure 11:
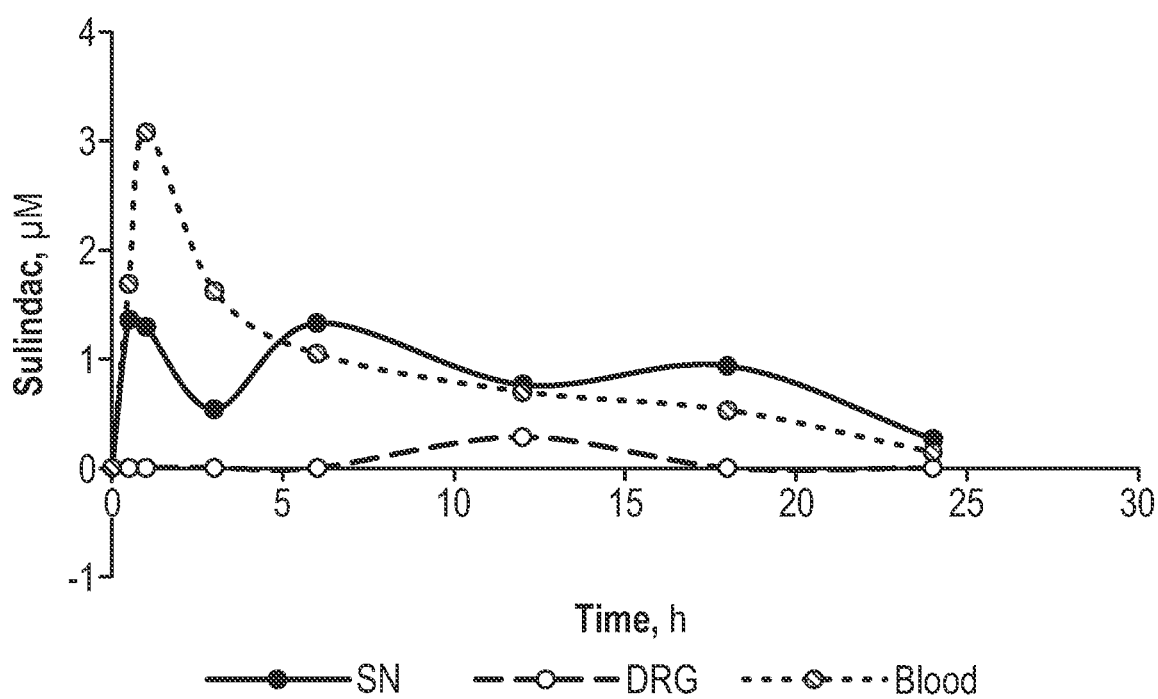

Only three metabolites of PS were detected: sulindac, sulindac sulfone, and sulindac sulfide, (FIG. 11 and Table 4). No glucuronidated products were detected. Sulindac was the quantitatively dominant metabolite, with sulindac sulfide and sulindac sulfone levels being <20% of those of sulindac. Sulindac levels were around 25% of those of PS in all tissues except the sciatic nerve (higher) and DRG (equal).

TABLE 4

PK parameters of sulindac in mouse tissue and peripheral blood of normal mice

| Tissue | $C_{max}$, µM mean ± SEM | $T_{max}$, h | $T_{1/2}$, h | $AUC_{0\text{-}24\,h}$, µM · h |
|---|---|---|---|---|
| Paw skin | 47.4 ± 3.8 | 0.5 | 47.4 | 516.6 |
| Paw muscle | 27.5 ± 3.3 | 0.5 | 7.9 | 238.6 |
| Leg muscle | 8.4 ± 2.1 | 0.5 | 8.2 | 71.8 |
| SN | 1.4 ± 0.3 | 0.5 | 12.3 | 22.3 |
| DRG | 0.3 ± 0.1 | 12 | * | 1.6 |
| Blood | 3.1 ± 0.5 | 1 | 6.2 | 21.2 |

* cannot be determined. N = 4-5 mice/time point.

The presence of PS even in small amounts in the sciatic nerve ($C_{max}$=0.9±0.1 µM; $AUC_{0\text{-}24\,h}$=12.0 µM·h) and DRG ($C_{max}$=0.3±0.1 µM; $AUC_{0\text{-}24\,h}$=4.5 µM·h) is of particular interest, since both are targets of chemotherapy associated with neuropathic pain. The absence of PS in the circulation, the very high $T_{max}$ of DRG compared to all others, and the lower levels of PS in DRG compared to the sciatic nerve suggest that PS reached the DRG by traversing from the skin through the sciatic nerve.

To further explore this conclusion, we compared the levels of PS in the proximal and distal half of the sciatic nerve of mice 30 min after its application to the hind paw. The two values were strikingly different, with those of the distal half being 18.5-fold higher than those of its proximal half (17±5.1 µM vs. 0.9±0.3 µM; Table 5). The concentration of the three metabolites of PS (sulindac, sulindac sulfide and sulindac sulfone) was also higher in the distal half compared to the proximal half (4.5-8.5-fold higher). These findings support the notion that PS reaches the DRG from the site of its application by direct tissue transfer or transport and not via the circulation.

TABLE 5

PS and its metabolites in the proximal and distal half of the sciatic nerve of mice

| | Distal | Proximal* µM, mean ± SEM | Fold difference |
|---|---|---|---|
| PS | 17.0 ± 5.1 | 0.9 ± 0.3 | 18.9 |
| Sulindac | 3.4 ± 1.1 | 0.4 ± 0.03 | 8.5 |
| Sulindac sulfide | 3.5 ± 1.0 | 0 | — |
| Sulindac sulfone | 0.9 ± 0.2 | 0.2 ± 0.08 | 4.5 |

*All differences between proximal and distal values are statistically significant (p < 0.001). N = 8 mice/group.

Conclusions

These experiments demonstrate that topically administered PS can reach key sites of action known to be involved in the generation of neuropathic pain associated with chemotherapy (i.e., the sciatic nerve and dorsal root ganglion). Furthermore, in light of its rapid metabolism in the bloodstream, the results demonstrate that PS reaches these sites of action by traversing along peripheral neurons (e.g., the sciatic nerve) towards the central nervous system, being found in meaningful concentrations in the DRG. Therefore, without wishing to be bound by theory, these observations confirm that PS likely performs its analgesic activity directly on neurons and likely within central sites of action, similar to the activity of centrally acting analgesics such as lidocaine and pregabalin.

Example 6 the Activity of PS in Treating and Preventing Neuropathic Pain Associated with CIPN is Equivalent to that of Lidocaine and Pregabalin, but Not Shared by Sulindac The effect of PS was compared to that of known central acting analgesics (lidocaine and pregabalin) and PS's parent compound, sulindac, on neuropathic pain associated with CIPN. The treatment of neuropathic pain associated with CIPN protocol corresponds to that explained in Examples 2 and 3.

Methods

The methods with respect to animals, induction of CIPN (with paclitaxel), assessment of mechanical allodynia and statistical analysis correspond to those outlined in Example 3.

CIPN was established by administration of paclitaxel into C57/BL/6J mice. The paclitaxel was administered into all study groups below:
1. Group 1: paclitaxel plus vehicle (n=8)
2. Group 2: paclitaxel plus PS 5% (n=8)
3. Group 3: paclitaxel plus PS 1.2% (n=8)
4. Group 4: paclitaxel plus 0.7% sulindac (n=8)
5. Group 5: paclitaxel plus 5% lidocaine cream (n=8)
6. Group 6: paclitaxel plus pregabalin (10 mg/kg) (n=8)

Regarding the treatment with PS, sulindac, and vehicle: PS hydrogel 5%, PS 1.2%, 0.7% sulindac, or vehicle, was applied to both hind paws 3 times a day starting on day 0 and continued until day 15. 0.7% sulindac is the highest feasible concentration, and is equimolar to PS 1.2%.

Regarding the treatment with lidocaine: 5% lidocaine cream (a positive control) was applied once to both hind paws of the mice 30 minutes before measurement of PWT.

Regarding the treatment with pregabalin: pregabalin at 10 mg/kg, (a positive control) was administered orally once, one hour before measurement of PWT.

To determine the outcome of treatment, assessment of mechanical allodynia was performed. Additionally, in the groups of mice treated with vehicle or PS 5%, assessment of cold allodynia (another manifestation of CIPN) was performed using the acetone test. Both methods of assessing allodynia are described in Toma W, et al. *Neuropharmacology* 2017; 117:305-15. Mechanical and cold allodynia are determined at least one day apart in the same animal.

Briefly, for mechanical allodynia, pain threshold responses were measured using the well-established method of von Frey filaments in line with that performed in the earlier Examples. The PWT test was performed on day-8 (before the first dose of paclitaxel), the day of starting treatment (day 0, at which CIPN was fully established) and day 14 (treatment continued until day 15). The mechanical threshold, expressed as g, indicates the force of the von Frey filament to which the animal reacted.

For cold allodynia, mice with paclitaxel-induced CIPN were treated with PS 5% or vehicle for 15 days after the induction of CIPN. The acetone test was used. Briefly, acetone was applied onto the plantar surface of each hind paw. The time each mouse spent licking, lifting, and/or shaking the hind paw recorded over 60 seconds was the score for cold allodynia. Measurements were performed on day-8 (before the first paclitaxel injection), the day of starting treatment (day 0) and then on day 15.

Results

As expected, paclitaxel induced CIPN, as demonstrated by the reduction of the mechanical allodynia from a score of 1.83±0.14 g prior to the administration of paclitaxel (Mean±SEM for this and all subsequent values), to 0.55±0.05 g on day 0 of the study (once CIPN was fully established). Paclitaxel also sensitized mice to cold allodynia, as evidenced by changes in its scores before and after paclitaxel treatment (4.5±0.24 sec vs. 7.1±0.4 sec; p<0.0001).

Figure 12A:
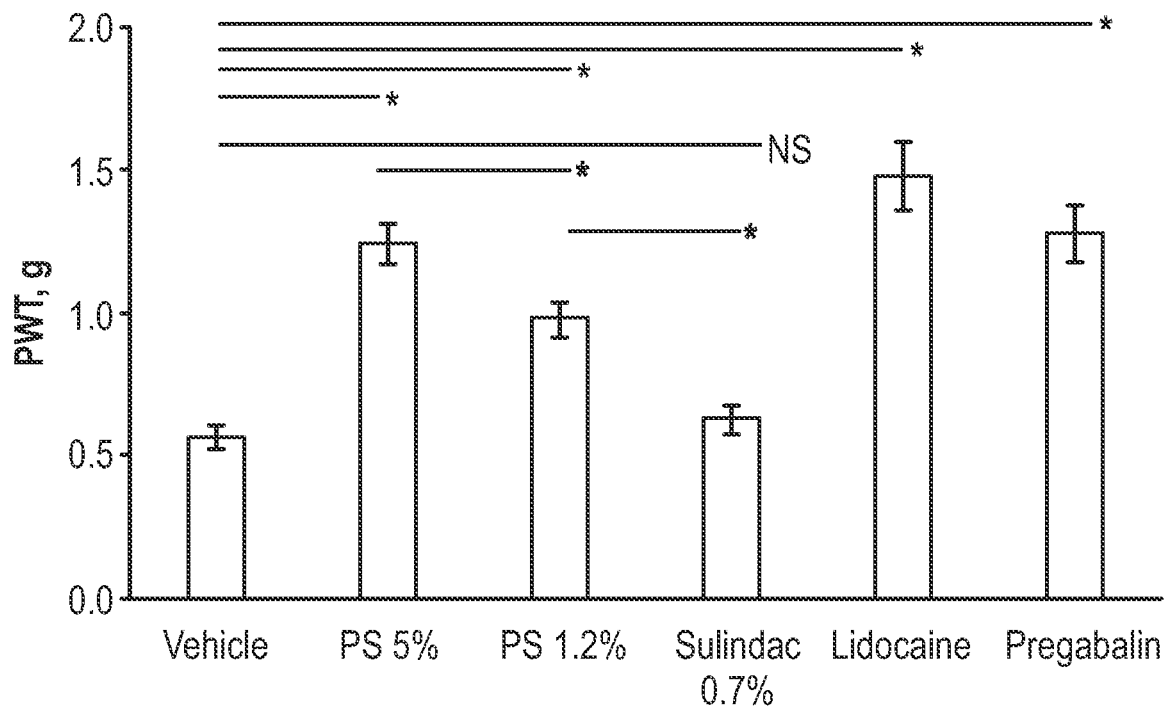
FIGS. 12A and 12B—effect of PS on treating neuropathic pain associated with CIPN compared to sulindac, lidocaine and pregabalin.
Figure 12B:
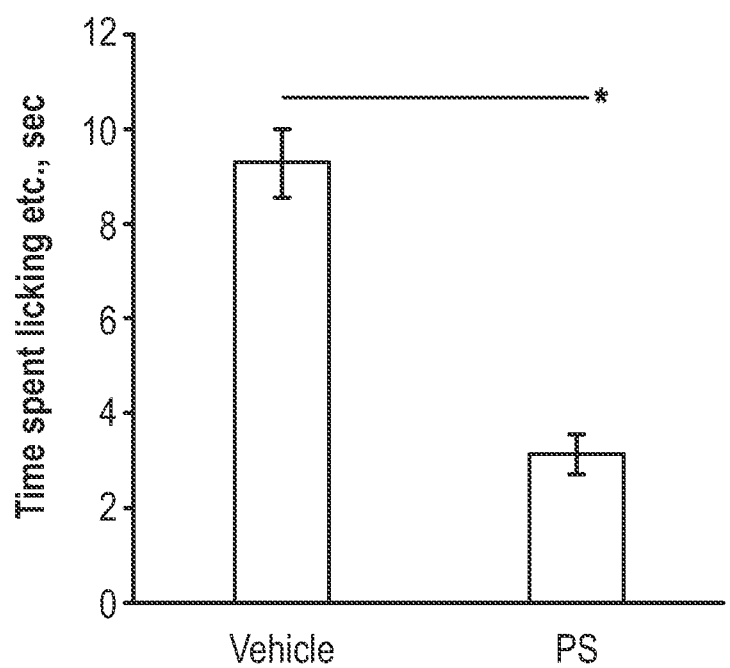

Treatment with PS improved the mechanical allodynia score in a dose-dependent manner (FIG. 12A). Likewise, treatment with PS 5% improved the cold allodynia score. The cold allodynia score of the PS-treated group was significantly lower than that of the vehicle-treated group (3.1±0.4 vs 9.3±0.7; p<0.0001) (FIG. 12B).

By contrast, administration of sulindac failed to demonstrate a significant effect on PWT, its score being similar to that of vehicle (0.62±0.05 g vs. 0.56±0.04 g; statistically not significant), while as expected both lidocaine and pregabalin positive controls achieved a significant increase in PWT compared to the vehicle (FIG. 12A). Importantly, PS 1.2%, a concentration that is equimolar to sulindac 0.7%, significantly improved mechanical allodynia (p<0.0001). The values concerning mechanical allodynia, corresponding to FIG. 12A, are provided in Table 6.

TABLE 6

PWT in the study groups

| Groups | PWT, g Mean ± SEM | P values |
|---|---|---|
| Paclitaxel + vehicle | 0.56 ± 0.04 | |
| Paclitaxel + PS 5% | 1.24 ± 0.07 | PS 5% vs. Vehicle: p < 0.0001 |
| Paclitaxel + PS 1.2% | 0.98 ± 0.06 | PS 1.2% vs Vehicle: p < 0.0001 PS 1.2% vs PS 5%: p < 0.008 |
| Paclitaxel + sulindac 0.7% | 0.62 ± 0.05 | Sulindac vs Vehicle: NS (p = 0.33) Sulindac vs PS 1.2%: p < 0.0001 |
| Paclitaxel + 5% lidocaine cream | 1.48 ± 0.12 | Lidocaine vs Vehicle: p < 0.0001 |
| Paclitaxel + pregabalin (10 mg/kg) | 1.28 ± 0.10 | Pregabalin vs Vehicle: p < 0.0001 |

Conclusions

Whereas PS was shown to be effective in the treatment and prevention of neuropathic pain associated with CIPN (see also Examples 1-3), strikingly its non-phosphorylated 'parent' sulindac (a typical NSAID) failed to achieve a rescue in the PWT in the mice model and so failed to treat neuropathic pain associated with CIPN. This was the case even though the sulindac was administered at a maximum non-toxic dose and in the same manner and formulation as PS. The positive controls, lidocaine and pregabalin, known to have central sites of action in analgesia, demonstrated a significant reduction in pain associated with CIPN, as expected. Therefore, the efficacy observed for locally administered PS is more similar to the centrally acting positive controls than to its closely related parent compound.

Accordingly, PS is mechanistically distinct from its parent NSAID and may be acting in a manner more similar to the centrally acting agents. These observations regarding the equivalent efficacy of PS and pregabalin and lidocaine in the treatment and prevention of neuropathic pain associated with CIPN reflect the central site of action of PS observed above (i.e., similar to that for pregabalin and lidocaine). These observations serve to demonstrate the potential of PS in the treatment of neuropathic pain associated with CIPN, akin to typical centrally acting analgesics (e.g., pregabalin and lidocaine).

Example 7 Summary of Observations

The observations herein demonstrate an unprecedented analgesic activity of PS in preventing and treating neuropathic pain associated with CIPN using a well-established animal model. Accordingly, the experiments above demonstrate that PS is able to reduce neuropathic pain signalling caused by CIPN, generated by a range of chemotherapeutic compounds. The mechanistic action of PS against mechanical allodynia is shown to affect pathophysiology common to each of the chemotherapeutic compounds—PS is having a direct effect on neuronal pain signalling generated by nerve damage caused by the chemotherapeutic compounds demonstrating the broad therapeutic applicability of PS in the treatment of neuropathic pain associated with chemotherapy. The therapeutic effect of PS on mechanical allodynia is very strong and fairly rapid via topical administration. Indeed, upon topical administration, PS is shown to follow an ascending trajectory along peripheral neurons (e.g., the sciatic nerve) towards the spinal cord and can achieve a significant analgesic effect in less than a week and lasting up to two weeks. The topical route provides low systemic clearance, reduced drug interactions, increased patient tolerability, and facile combination with oral medications.

These observations demonstrate a previously unrecognised activity and therapeutic utility of PS, a compound which falls within the broader class of NSAIDs but does not share all of the properties of this family of compounds. In fact, in contrast to previous observations for NSAIDs, the data herein demonstrate that the activity of PS is more similar to analgesic agents which target neuronal activity directly, and with potential to act at both peripheral and central sites. Indeed, the results above confirm that PS can reduce pain from allodynia which is known to include pain generated via peripheral and central sensitisation. In the CIPN treatment model, pain was established for five days prior to treatment randomisation thus establishing central sensitisation demonstrated by the allodynia (compared to the baseline). Therefore, without wishing to be bound by theory, PS is having a direct effect on neuronal pain signalling, similar to the mechanism of action of established anaesthetics. In fact, the results show the ability of PS to reduce pain signalling from peripheral and central sensitisation, implicating both peripheral and central sites of action for the analgesic activity of this compound. Of course, this activity is distinct from the established role of PS, and typical NSAIDs, as anti-inflammatory agents.

Earlier observations regarding the activity of PS are limited to its anti-inflammatory activity. For example, WO 2019/067919 suggests a role for PS in the treatment of DED, using an acute DED model, in which concanavalin A (ConA) is administered to rabbit lacrimal glands concurrently with PS. In this context, the anti-inflammatory activity of PS results in a limited inflammatory response to ConA, thus preventing the establishment of DED. These observations confirm the anti-inflammatory activity of PS and suggest its utility in preventing establishment and maintenance of inflammatory components of DED. The observations in this acute DED model fail to provide any evidence of the ability of PS to act directly on nerves to reduce nerve signalling caused by neuropathic pain. Any reduction in pain in this acute DED model can be assumed only to be a consequence of PS inhibiting the inflammatory response (i.e., the pathology responsible for triggering activation of the pain sensors). In fact, the results of the DED model suggest that PS improves corneal sensitivity, implicating an increase in nociception, the opposite effect to that desired for an analgesic. Of course, irrespective of any suggestion towards analgesic activity of PS, such activity observed in an acute DED model provides no indication of a corresponding activity in neuropathic pain, and certainly not in neuropathic pain associated with CIPN.

The experiments herein were performed in a specific animal model for neuropathic pain associated with CIPN. As outlined above, the use of appropriate animal models is critical for demonstrating the potential efficacy of a compound in a particular type of neuropathic pain. Efficacy of a drug against pain arising from peripheral neuropathies cannot be extrapolated from its efficacy against other forms of pain, or even other forms of neuropathic pain. Indeed, specific forms of neuropathic pain differ in their pathogenesis and thus require therapeutic agents with different activities for their treatment and/or prevention. Therapies need to be designed according to the specific pathophysiology of the neuropathic pain and tested in an appropriate model. For example, CIPN causes direct nerve damage to sensory axons, demyelination or impairment of calcium metabolism due to administration of toxic chemotherapeutic agents, while other neuropathies may occur as a result of extensive nerve damage by metabolic abnormalities (e.g., as seen in diabetic peripheral neuropathy). Therefore, the effects on both large and small fibres differs between CIPN and other forms of neuropathy on the basis of their specific pathophysiology. The only reliable determination of efficacy of a compound in treating the neuropathic pain caused by such pathophysiology is to test the compound in an appropriate neuropathic pain model of CIPN, as shown above. Without these observations, any indication of pain relieving activity of PS in the context of neuropathic pain associated with CIPN is lacking.

The observations herein demonstrate that PS has therapeutic utility beyond that suggested for typical NSAIDs. Such NSAIDs, for example loxoprofen sodium, are ineffective in reducing pain signalling in paclitaxel induced CIPN. Furthermore, Moore et al. (Cochrane Database of Systematic Reviews (2015); 10: 1-25), outlined that NSAIDs have no therapeutic efficacy in peripheral neuropathic pain. The activity of PS observed herein, corresponding to that of pregabalin and lidocaine, contrasts with the inability of typical NSAIDs to provide a direct analgesic effect on damaged neurons in neuropathic pain as observed in the prior art. The distinct activity of PS compared to typical NSAIDs is confirmed by the comparison with its parent compound, sulindac, in the experiments above. Sulindac failed to reduce established allodynia (i.e., caused by sensitisation of peripheral and central neurons), indicating that, unlike PS, sulindac does not provide a direct analgesic effect on damaged neurons in neuropathic pain caused by CIPN. Without wishing to be bound by theory, the reason for the absence of any response to typical NSAIDs in the prior art is likely that the pain is caused by neuropathic nerve damage, rather than by inflammation (i.e., any anti-inflammatory activity of typical NSAIDs is not sufficient to prevent or treat the neuropathic pain). Accordingly, the analgesic activity of PS observed herein is unique and not shared by typical NSAIDs. Based on the observations herein for sulindac, any alleged analgesic activity of NSAIDs observed in the prior art is a reflection of their anti-inflammatory activity (i.e., stopping the initial triggers causing the pain) rather than an actual analgesic activity directed towards nerve signalling (i.e., that would result in a reduction in pain caused by nerve damage and sensitisation). Indeed, if typical NSAIDs, for example sulindac, were capable of acting directly on neurons with analgesic activity, then sulindac would have been expected to reduce the allodynia observed in the model above.

Therefore, the present inventor has demonstrated a new surprising activity for PS in the treatment and/or prevention of neuropathic pain associated with CIPN. As outlined above, this activity goes beyond the anti-inflammatory activity previously observed for PS and related NSAIDs. In fact, unlike typical NSAIDs, the observations herein demonstrate that PS has a direct activity on peripheral and central nerves, likely similar to the site and mechanism of action of established analgesics, such as lidocaine and pregabalin. Furthermore, the ease by which PS can be administered, for example topically, and its limited adverse effects (Mackenzie et al. (2010) *Gastroenterology* 139(4): 1320-32) render it an improved therapy for neuropathic pain associated with CIPN compared even to these centrally acting analgesics.

It will be understood that the inventor's work has been described above by way of example only and modifications may be made while remaining within the scope and spirit of the invention.

The invention claimed is:

1. A method of treating and/or preventing neuropathic pain associated with chemotherapy induced peripheral neuropathy (CIPN) comprising administering a therapeutically effective amount of phosphosulindac (PS) to a subject in need thereof such that neuropathic pain associated with CIPN is treated and/or prevented.

2. The method of claim 1, wherein treating the neuropathic pain comprises reducing or eliminating the neuropathic pain, or reducing or eliminating one or more of the sensory symptoms associated with CIPN.

3. The method of claim 1, wherein preventing the neuropathic pain comprises decreasing the incidence of the neuropathic pain, or decreasing the incidence of one or more of the sensory symptoms associated with CIPN.

4. The method of claim 2, wherein the one or more sensory symptoms is selected from paresthesia, burning sensations and shooting sensations.

5. The method of claim 4, wherein the paresthesia includes one or more of numbness, tingling, pricking, or formication.

6. The method of claim 1, wherein PS reduces, eliminates, or decreases the incidence of the neuronal signalling involved in the sensation of pain, or the incidence of pain generated via peripheral sensitisation, or the incidence of pain generated via central sensitisation, or the incidence of pain signalling occurring centrally, or the incidence of pain signalling occurring in the sciatic nerve, or the incidence of pain signalling occurring in the dorsal root ganglion.

7. The method of claim 1, wherein the neuropathic pain is allodynia.

8. The method of claim 7, wherein the allodynia is mechanical allodynia and/or thermal allodynia.

9. The method of claim 1, wherein the neuropathic pain is hyperalgesia.

10. The method of claim 1, wherein the subject has cancer and is receiving or has been previously treated with one or more chemotherapeutic compounds.

11. The method of claim 10, wherein the one or more chemotherapeutic compounds is selected from one or more of platinum-based drugs, taxanes, immunomodulatory drugs, epothilones, vinca alkaloids, and proteasome inhibitors.

12. The method of claim 11, wherein the one or more chemotherapeutic compounds is selected from one or more of oxaliplatin, cisplatin, carboplatin, taxane, paclitaxel, docetaxel, cabazitaxel, thalidomide and its analogues, vincristine, vinblastine, vinorelbine, vindesine, and bortezomib.

13. The method of claim 10, wherein the chemotherapeutic compound is a taxane.

14. The method of claim 10, wherein the chemotherapeutic compound is a vinca alkaloid.

15. The method of claim 10, wherein the chemotherapeutic compound is a platinum-based antineoplastic.

16. The method of claim 10, wherein the subject has a solid tumor cancer.

17. The method of claim 10, wherein the subject has ovarian cancer, breast cancer, lung cancer, Kaposi sarcoma, and/or pancreatic cancer.

18. The method of claim 1, wherein the subject is human.

19. The method of claim 1, wherein PS has the formula I (PS-I):

(I)

20. The method of claim 1, wherein PS has the formula II (PS-II):

(I)

21. The method of claim 1, wherein the therapeutically effective amount of PS is administered as a pharmaceutical composition comprising PS and a pharmaceutically acceptable excipient.

22. The method of claim 21, wherein the pharmaceutical composition comprising PS is formulated for topical administration.

23. The method of claim 22, wherein the pharmaceutical composition comprising PS is formulated as a semi-solid.

24. The method of claim 22, wherein the pharmaceutical composition comprising PS is formulated as a liquid.

25. The method of claim 22, wherein the pharmaceutical composition comprising PS is a cream, a gel, a hydrogel, a lotion, an ointment, or a spray.

26. The method of claim 22, wherein the pharmaceutical composition comprising PS is formulated as a patch.

27. The method of claim 21, wherein the pharmaceutical composition comprises PS at a concentration of about 0.5% to about 15% w/w of the pharmaceutical composition.

28. The method of claim 27, wherein the pharmaceutical composition comprises PS at a concentration of about 15%, 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, 1%, or 0.5% w/w of the pharmaceutical composition.

29. The method of claim 28, wherein the pharmaceutical composition comprises PS at a concentration of less than or equal to 8% w/w of the pharmaceutical composition.

30. The method of claim 28, wherein the pharmaceutical composition comprises PS at a concentration of less than or about equal to 3% w/w of the pharmaceutical composition.

31. The method of claim 21, wherein the PS is administered at about 0.005 g/10 cm$^2$ to about 0.25 g/10 cm$^2$ of affected area.

32. The method of claim 31, wherein the PS is administered at about 0.005 g/10 cm$^2$ of affected area, or at about 0.01 g/10 cm$^2$ of affected area, or at about 0.05 g/10 cm$^2$ of affected area, or at about 0.1 g/10 cm$^2$ of affected area, or at about 0.15 g/10 cm$^2$ of affected area, or at about 0.2 g/10 cm$^2$ of affected area, or at about 0.25 g/10 cm$^2$ of affected area.

33. The method of claim 21, wherein the PS is applied to an affected area and left on the affected area for between about 1 hour and about 5 hours.

34. The method of claim 33, wherein the PS is applied to an affected area and left on the affected area for about 0.5 hours, for about 1 hour, for about 2 hours, for about 3 hours, for about 4 hours, or for about 5 hours.

35. The method of claim 33, wherein the PS is removed from the affected area after being left on the affected area for between about 1 hour and about 5 hours.

36. The method of claim 33, wherein a second or further application of PS is applied to the affected area.

37. The method of claim 21, wherein the PS is applied once a day, twice a day, three times a day, or four times a day.

\* \* \* \* \*